(12) United States Patent
Sedelmeier

(10) Patent No.: US 8,569,528 B2
(45) Date of Patent: Oct. 29, 2013

(54) PROCESS FOR THE PREPARATION OF TETRAZOLE DERIVATIVES FROM ORGANO BORON AND ORGANO ALUMINIUM AZIDES

(75) Inventor: Gottfried Sedelmeier, Schallstadt (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/603,770

(22) Filed: Sep. 5, 2012

(65) Prior Publication Data

US 2012/0330026 A1    Dec. 27, 2012

Related U.S. Application Data

(60) Continuation of application No. 13/081,881, filed on Apr. 7, 2011, now abandoned, which is a division of application No. 10/564,337, filed as application No. PCT/EP2004/007980 on Jul. 15, 2004, now Pat. No. 7,943,647.

(30) Foreign Application Priority Data

Jul. 15, 2003    (GB) ................... 0316546.1

(51) Int. Cl.
C07F 5/02    (2006.01)
C07F 5/06    (2006.01)

(52) U.S. Cl.
USPC ............................................. 552/4

(58) Field of Classification Search
USPC ............................................. 552/4
See application file for complete search history.

(56) References Cited

U.S. PATENT DOCUMENTS

| | | |
|---|---|---|
| 2,977,372 A | 3/1961 | Finnegan et al. |
| 3,394,142 A | 7/1968 | Koshar |
| 4,097,479 A | 6/1978 | Leipzig |
| 4,122,274 A | 10/1978 | Juby |
| 4,213,986 A | 7/1980 | Gebert et al. |
| 4,338,452 A | 7/1982 | Katner |
| 4,372,953 A | 2/1983 | Uchida et al. |
| 4,820,843 A | 4/1989 | Aldrich et al. |
| 4,831,192 A | 5/1989 | Lin et al. |
| 4,870,186 A | 9/1989 | Aldrich et al. |
| 4,874,867 A | 10/1989 | Aldrich et al. |
| 5,128,355 A | 7/1992 | Carini et al. |
| 5,138,069 A | 8/1992 | Carini et al. |
| 5,153,197 A | 10/1992 | Carini et al. |
| 5,155,118 A | 10/1992 | Carini et al. |
| 5,196,444 A | 3/1993 | Naka et al. |
| 5,210,079 A | 5/1993 | Carini et al. |
| 5,254,543 A | 10/1993 | Hanko et al. |
| 5,256,658 A | 10/1993 | Hsi et al. |
| 5,270,317 A | 12/1993 | Bernhart et al. |
| 5,270,322 A | 12/1993 | Ries et al. |
| 5,371,233 A | 12/1994 | Daumas et al. |
| 5,399,578 A | 3/1995 | Buhlmayer et al. |
| 5,447,949 A | 9/1995 | Girard et al. |
| 5,502,191 A | 3/1996 | Galante |
| 5,559,233 A | 9/1996 | Bernhart et al. |
| 5,591,762 A | 1/1997 | Hauel et al. |
| 5,594,003 A | 1/1997 | Hauel et al. |
| 5,602,127 A | 2/1997 | Hauel et al. |
| 5,608,075 A | 3/1997 | Campbell, Jr. et al. |
| 5,614,519 A | 3/1997 | Hauel et al. |
| 5,705,517 A | 1/1998 | Naka et al. |
| 6,156,906 A | 12/2000 | Hyoda et al. |
| 6,362,210 B1 | 3/2002 | Hauel et al. |
| 2004/0062283 A1* | 4/2004 | Takeuchi et al. ............ 372/45 |
| 2004/0072886 A1 | 4/2004 | Reguri et al. ............ 514/381 |

FOREIGN PATENT DOCUMENTS

| | | |
|---|---|---|
| CA | 2154807 | 2/1996 |
| EP | 0 016 662 | 10/1980 |
| EP | 0 039 913 | 11/1981 |
| EP | 0 253 310 | 1/1988 |
| EP | 0 286 296 | 3/1988 |
| EP | 0 291 969 | 11/1988 |
| EP | 443 983 B1 | 2/1991 |
| EP | 0 459 136 A1 | 4/1991 |
| EP | 0 459 136 | 12/1991 |
| EP | 502 314 B1 | 1/1992 |
| EP | 0 557 843 A2 | 2/1992 |
| EP | 0502 317 | 9/1992 |
| EP | 0 536 400 | 4/1993 |
| EP | 0 796 852 A1 | 9/1997 |
| EP | 0 796 852 B1 | 9/1997 |
| EP | 0578125 | 4/1998 |
| EP | 1 016 662 A1 | 7/2000 |
| EP | 0120483 | 11/2008 |
| JP | AH0673028 | 3/1994 |
| JP | 06107658 | 4/1994 |
| JP | A-4-235149 | 3/1995 |
| JP | A-60-73028 | 4/1998 |

(Continued)

OTHER PUBLICATIONS

Joseph et al., "3-Aryl-2-Quinolone Derivatives: Synthesis and Characterization of In Vitro and In Vivo Antitumor Effects with Emphasis on a New Therapeutical Target Connected with Cell Migration," J. Med. Chem., vol. 45, pp. 2543-2555 (2002).
Wazir et al., "Synthesis and Anti-Inflammatory Activity of Some Substituted Tetrazoles," J. Ind. Chem. Soc., vol. 68(5), pp. 305-306 (1991).
Aleksanyan et al., "Synthesis of 5-Substituted N(1)- and N(2)- Tetrazoiylacetic Acids and Their Biologicai Propetties," Khimiko-Farmatsevticheskii Zhurnal, vol. 24(10), pp. 56-58 (1990).
Ostrovskii et al., "Tetrazoles. 31. Kinetics of the Reaction of Nitriles with Alkylammonium Azides, Formation of 5-Substituted Tetrazoles," Khimiya Geterotsikiicheskikh Soedinenii, vol. 9, pp. 1027-1030 (1993).
Demko et al., "Simple Preparation of 5-Substituted-1H-tetrazoles from nitriles in water and related mechanistic studies," Abstract 626 (2001).
Candesartan cilexcetil (product), Patent information.
Irbesartan (product), Patent Information.
Losartan (product), Patent Information.
Valsartan (product), Patent information.

(Continued)

*Primary Examiner* — Shawquia Young
(74) *Attorney, Agent, or Firm* — Matthew Mulkeen

(57) ABSTRACT

The present invention relates to a method for preparing substituted tetrazoles, compounds obtained according to this method, new reactants and new tetrazole derivatives.

7 Claims, No Drawings

(56) References Cited

FOREIGN PATENT DOCUMENTS

| | | |
|---|---|---|
| JP | 10-218868 | 8/1998 |
| JP | 2000-281662 | 10/2000 |
| SU | 497775 | 6/1976 |
| WO | WO 92/10189 | 6/1992 |
| WO | 9304052 | 3/1993 |
| WO | WO 93/04046 | 3/1993 |
| WO | WO9314086 | 7/1993 |
| WO | WO9407872 | 4/1994 |
| WO | 95/26346 | 10/1995 |
| WO | 96/37481 | 11/1996 |
| WO | WO 01/23442 | 4/2001 |
| WO | 2004/026847 | 4/2004 |
| WO | WO 2005/090644 | 9/2005 |

OTHER PUBLICATIONS

Eicher et al., "The Chemistry of Heterocycles." Georg Thieme Verlag, Stuttgart, NY, p. 215 (1995).

Youn, Y.S. et al, Lithium azidohydridodiisobutylaluminate in THF as an efficient azide donor, 1998, vol. 39, No. 24, p. 4337-8.

Meier, H.U. et al, Iminoboranes from the thermal decomposition of dialkylazidoboranes, Chemische Berichte, 1984, vol. 117, No. 5, p. 1954-65.

Paetzold, P. et al, Boron imides in the thermal decomposition of diary lazidoboranes, Chemische berichte, 1983, vol. 116, No. 4. p. 1531-1539.

Paetzold, P.I. et al, Chemistry of boron azides VII. Preparation and properties of diorganylboron azides. The Journal of Organometallic Chemistry, 1967, vol. 7, No. 1, p. 45-50.

Paelzold, P.I. et al, Chemistry of boron azides. VIII. Thermal decomposition of diorganylboron azides. Journal of Organometallic Chemistry, 1967, vol. 7, No. 1, p. 51-60.

Paelzold, P.I. et al, Chemistry of boron azides. IX. Migratory aptitudes, kinetics, and mechanism of the thermal rearrangement of diorganylboron azides. Journal of Organometallic Chemistry, 1967, vol. 7, No. 1, p. 61-70.

Behringer, Hans et al., Ueber Tetrazole, I. Mitteil: Die Synthese des 5-[Amino-aethyl] tetrazols . . . , Chemische Berichte, vol. 89, issue 11, pp. 2648-26536, 24, Aug. 1956 (German, English abstract).

Ellis, P and Shaw, D., "Benzopyrones. 7. Synthesis and antiallergic activity of some 2-(5-tetrazolyl) chromones." Journal of Medicinal Chemistry vol. 15, No. 8, p. 865, 1972.

Eicher, Theophil and hauptmann Siegfried, The Chemistry of Heterocycles, Structure, Reactions, Syntheses and Applications, Georg Thieme Verlag Stuttgart—New York , Tetrazole, p. 215. (1995).

Himo et al. "Mechanisms of Tetrazole Formation by Addition of Azide to Nitrites", JACS, Sep. 19, 2002.

Chadwick and Sharpe "Advances in inorganic chemistry and radiochemistry". Academic press 1966, pp. 140 on line.

Harris "Quantitative Analysis" pp. 348. Table 16.1.

Demko et al., "Preparation of 5-Substituted 1H-Tetrazoles from Nitrites in Water," J. Org. Chem., vol. 66, pp. 7945-7950 (2001).

Demko et al., "A Click Chemistry Approach to Tetrazoles by Huisgen 1.3-Dipolar Cycloaddition: Synthesis of 5-Acyltetrazoles from Azides and Acyl Cyanides," Angew. Chem. Int. Ed., vol. 41(12), pp. 2113-2116 (2002).

Demko et al., "A Click Chemistry Approach to Tetrazoles by Huisgen 1,3-Dipolar Cycloaddition: Synthesis of 5-Sulfonyl Tetrazoles from Azides and Sulforiyl Cyanides," Angew. Chem. Int. Ed., vol. 41(12), pp. 2110-2113 (2002).

Amantini et al., "TBSF-Catalyzed Synthesis of 5-Substituted 1H-Tetrazoles under Solventless Conditions," J. Org. Chem., vol. 69(8), pp. 2896-2898 (2004).

Munoz-Hernandez et al., "Examination of dibenzyl aluminum and gallium azides as potential precursors to AIN and GaN," Journal of Organometallic Chemistry, vol. 582(1), pp. 193-107 (1999).

Berlin et al., The Condensation of Diphenylphosphinic Acide with Substituted Acetonitriles—Formation of Phosphorylated tetrazolines (I); Journal of Heterocyclic Chemistry, vol. 5(6). pp. 813-823 (1968).

Hagishita et al., "Potent Inhibitors of Secretory Phospholipase A2: Synthesis and Inhibitory Activities of Indolizine and Indene Derivatives," vol. 39(19), pp. 3636-3658 (1996).

Curran et al., "tri(2-Perfluorohexylethyl)tin acide: A New Reagent for Preparation of 5-substituted Tetrazoles from Nitriles with Purification by Fluorous/Organic Liquid-Liquid Extraction," Tetrahedron, vol. 55, pp. 8997-9006 (1999).

Koguro et al., "Novel Synthesis of 5-Substituted Tetrazoles from Nitriles," Synthesis, vol. 6, pp. 910-914 (1998).

Jursic et al., "Preparation of Tetrazoles from Organic Nitriles and Sodium Acide in Micellar Media," J. Heterocyclic Chem., vol. 35(2), pp. 405-408 (1998).

Wittenberger et al., "Dialkyltin Oxide Mediated Addition of Trimethylallyl Azide to Nitriles. A Novel Preparation of 5-Substituted Tetrazoles." J. Org. Chem., vol. 58(15), pp. 4139-4141, (1993).

Shukla et al., "Synthesis and Anti-Inflammatory Activity of Some 5-Substituted Tetrazoles," Current Science, vol. 56(14), pp. 709-710 (1987).

Kevill et al., "Synthesis of 5-Substituted 1-(1-Adamiantyl)tetrazoles and Related Compounds," J. Org. Chem., vol. 35(5), pp. 2526-2529 (1970).

Finnegan et al., "An Improved Synthesis of 5-Substituted Tetrazoles," J. Am. chem. Soc., vol. 80, pp. 3908-3911 (1958).

J. Organometal Chem. 5, 1966 pp. 584-586.

Bull. Korean Chem. Soc. vol. 9 No. 4, 1988, 269-270.

Tetrahedron letters, vol. 35, No. 28, pp. 4947-4950, 1994.

Journal of the American Chemical Society, 94:6, Mar. 22, 1972, pp. 2114-2115.

Chapman & Hall, Blackie Academic & Professional, A.J. Downs, Chemistry of Aluminium. Gallium, Indium and Thallium, pp. 457-459, (1993).

R.L. Mulinax et al, J. Phys. Chem., 1995, 99, pp. 6294-6300.

Khimiya Geterotsiklicheskikh Soedinenii 1992, 9, 1214-1217.

Abstract: Organoboranes—New Chemistry and Mechanisms Nov. 2000 http://scirus.com/srapp/search?q=Organoboranes.

Bradbury R.H. et al., J. Med. Chem. 1992, vol. 35, No. 22, pp. 4027-4036.

Arnold C. et al., J. Org. Chem., 1969, vol. 34, No. 4, pp. 1141-1142.

The fourth Series of Experimental Chemistry, 1991. vol. 24, p. 100 (1 page for JP ref. and 3 pages for the English translation).

Pfizer Corp. AU 8656-100-A: New benzothiazine-dioxide cpd. 5 lipoxygenose inhibitors useful in treating allergic asthma and adult repiratory distress syndrome, etc.: Derwent Publications, Ltd. , (2004).

Ciba Geigy, AG; SU-497-775: Tetrazole derivatives preparation, Derwent Publications, Ltd (2004).

Demko, Z. et al; "Simple preparation of 5-substituted 1H tetrazoles from nitriles in water and related mechanistic studies"; Abstracts of papers, American Chemical Society (2001).

March, J. Advanced Organic Chemistry, Reactions, Mechanism, and Structure, John Wiley & Sons, $3^{rd}$ edition, p. 1057 (1985).

Shukla et al., "Synthesis of Some Newer 5-Substituted Tetrazoles as Anti-Inflammatory Agents," Indian Drugs, vol. 184, pp. 138-141 (1981).

Shukla et al., "Synthesis and Anti-inflammatory Activity of Some Substituted Tetrazoles," Indian Journal of Pharmaceutical Sciences, vol. 41(2), pp. 70-71 (1979).

"Kinetics of the Reaction of Nitriles With Alkylammonium Azides, Formation of 5-Substituted Tetrazoles", Khimiya Geterotsiklicheskikh Soedineniy, 1992, (9), 1214-1217.

Facile Reaction of Dialkylchloroboranes with Organic Azides. A Remarkable Enhancement of Reactivity Relative to Trialkylboranes:, Journal of the American Chemical Society, Mar. 22, 1972, 94:6, pp. 2114-2115.

(56) References Cited

OTHER PUBLICATIONS

Downs, A. J., Chemistry of Aluminum, Gallium, Indium and Thallium, Blackie Academic & Professional, an Imprint of Chapman & Hall, 1993, pp. 457-459.

Mulinax, R. L. et al., "Gas Phase Synthesis, Structure, and Dissociation of Boran Triazide", J. Phys. Chem., 1995, vol. 99, pp. 6294-6300.

http://www.cs.utexas.edu/ftp/pub/inderjit/Data/Text/NSFAII/Abstracts/abstracts/CHE.MPS.a8706102.txt, "Organoborones—New Chemistry and Mechanisms" Abstracts, 2000.

Himo, Fahmi et al., "Why is Tetrazole Formation by Addition of Azide to Organic Nitrates Catalyzed by Zinc(II) Salts?", J. Am. Chem. Soc., 2003, 125, pp. 9983-9987.

* cited by examiner

PROCESS FOR THE PREPARATION OF TETRAZOLE DERIVATIVES FROM ORGANO BORON AND ORGANO ALUMINIUM AZIDES

This application is a continuation of U.S. patent application Ser. No. 13/081,881, filed Apr. 7, 2011, which is a divisional of U.S. patent application Ser. No. 10/564,337, filed Aug. 11, 2006, which is a National Phase Application of International application No. PCT/EP2004/007980, filed Jul. 15, 2004, which claims benefit of GB 0316546.1, filed Jul. 15, 2003.

The invention relates to a method for preparing substituted tetrazoles, compounds obtained according to this method, new reactants and new tetrazole derivatives.

Tetrazoles are structural elements, for example, of pharmaceuticals or agricultural compositions, foaming agents, automotive inflators, and the like. Especially mentioned are the class of so-called angiotensin II receptor antagonists also designated nowadays as angiotension receptor blockers (ARBs) that can be used e.g. for the treatment of hypertension and congestive heart failure. Most of said ARBs comprise as structural element a 5-tetrazole group.

It is known in the art that tetrazole derivatives can be prepared by reacting various nitriles with organic azides in relatively good yields. Representatives of corresponding azides are, for example, organo-tin azides which have some toxic profile. They have to be handled with special care in production processes, cause ecological problems and require a significant amount of additional process work to recycle them from the wastewater thereby additionally increasing the production costs. Tetrazole forming methods which use trialkylammonium azides or tetraalkylammonium azides may form volatile sublimates in the reaction reactors at higher temperatures which have the risk of explosion and are therefore not easy to handle in large scale production.

There is a strong need to develop process variants, new reagents and intermediates that avoid the above-mentioned disadvantages. Especially, a lot of effort has been made to substitute corresponding organo-tin azides with alternative agents which are viable alternatives in the production of tetrazoles with sufficiently high yields.

It has surprisingly been found that organo boron azides and organo aluminium azides can be used as alternatives to corresponding organo-tin compounds. Said boron and aluminium compounds are available in considerably large scales and are relatively inexpensive, especially corresponding aluminium compounds that are produced for the polymer industry (e.g. Ziegler-Natta catalysis). It has surprisingly turned out that high yields of tetrazoles can be achieved when using these organo azides to be used according to the present invention. Furthermore, as the corresponding boron and aluminium azides are not known to be toxic, their use does not require special care when recycling the waste water and moreover the dialkylmetal azides can be produced in a large scale at low costs and mild conditions. Even though, corresponding dialkyl boron and dialkyl aluminium azides have these advantages, they have not been described in the literature to be used in [2+3]cycloadditions with nitriles to form tetrazoles. What is known from the literature is that e.g. di-organyl aluminium azides can be used to open epoxides and also to form acylazides from esters. However, the use of di-organyl boron or di-organyl aluminium azides, respectively, to form tetrazoles with nitriles is fully surprising.

The present invention relates to the use of organo boron and organo aluminium azides, especially as defined below, for the manufacture of tetrazole derivatives.

The present invention relates to a process for the manufacture of a tetrazole of formula

or a tautomer or a salt thereof, wherein R represents an organic residue; comprising
(i) reacting a compound of formula R—CN (II a) with an azide of formula $(R_1)(R_2)M-N_3$ (II b), wherein R has the meaning as defined above; $R_1$ and $R_2$, independently of another, represent an organic residue such as an aliphatic residue, an alicyclic residue, a heteroalicyclic residue; an alicyclic-aliphatic residue; a heteroalicyclic-aliphatic residue; a carbocyclic or a heterocyclic aromatic residue; an araliphatic residue or an heteroaraliphatic residue, each residue, independently of another, being unsubstituted or substituted; and M is boron or aluminium; and
(ii) isolating the resulting compound of formula (I).

A tautomer of a compound of formula (I) is a compound of formula

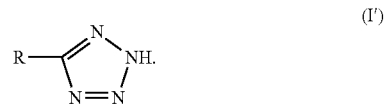

A salt of a compound of formulae (I) or (I'), if the compounds of formulae (I) or (I') have, for example, at least one basic centre, can be an acid addition salt. This is formed, for example, with a strong inorganic acid, with a strong organic carboxylic acid, or with an organic sulfonic acid. A corresponding acid addition salt can also be formed, if desired, with any additionally present basic centre. If the compounds of formulae (I) or (I') have at least one acid group (for example COOH or 5-tetrazolyl) a salt with a base can be formed. A suitable salt with bases is, for example, metal salts, or a salt with ammonia or an organic amine. A corresponding internal salt may furthermore be formed.

The general definitions used above and below of the corresponding residues, unless otherwise defined below, have the following meanings:

An organic residue is, for example; an aliphatic residue, an alicyclic residue, a heteroalicyclic residue; an alicyclic-aliphatic residue; a heteroalicyclic-aliphatic residue; a carbocyclic or a heterocyclic aromatic residue; an araliphatic residue or an heteroaraliphatic residue, each residue, independently of one another, being unsubstituted or substituted.

An aliphatic residue is, for example, alkyl, alkenyl or secondarily alkynyl, each of which can be interrupted by NH, substituted NH, O, or S; and each of which can be unsubstituted or substituted, for example, mono-, di- or tri-substituted.

Alkyl is, for example, $C_1$-$C_{20}$-alkyl, in particular $C_1$-$C_{10}$-alkyl. $C_1$-$C_8$-alkyl is preferred, for example methyl, ethyl, n-propyl, isopropyl, n-butyl, isobutyl or tert-butyl.

Alkenyl is, for example, $C_3$-$C_{20}$-alkenyl, in particular $C_3$-$C_{10}$-alkenyl. Preferred is $C_3$-$C_5$-alkenyl; for example, 2-propenyl or 2- or 3-butenyl. Alkenyl is likewise $C_2$-$C_{20}$-alkenyl, in particular $C_2$-$C_{10}$-alkenyl. Preferred is $C_2$-$C_5$-alkenyl.

Alkinyl is, for example, $C_3$-$C_{20}$alkynyl, in particular $C_3$-$C_{10}$alkynyl. Preferred is $C_3$-$C_5$alkynyl such as propargyl. Alkinyl is likewise $C_2$-$C_{20}$alkynyl, in particular $C_2$-$C_{10}$alkynyl. Preferred is $C_2$-$C_5$alkynyl.

Alkyl, alkenyl or alkynyl that can be interrupted by NH, substituted NH, O or S is in particular $C_1$-$C_{20}$-alkoxy-$C_1$-$C_{20}$-alkyl, —$C_3$-$C_{20}$-alkenyl or —$C_3$-$C_{20}$-alkynyl, or $C_3$-$C_{20}$-alkenyloxy-$C_1$-$C_{20}$-alkyl, —$C_3$-$C_{20}$-alkenyl or —$C_3$-$C_{20}$-alkynyl, for example, $C_1$-$C_{10}$-alkoxy-$C_1$-$C_{10}$-alkyl, —$C_3$-$C_{10}$-alkenyl or —$C_3$-$C_{10}$-alkynyl, or $C_3$-$C_{10}$-alkenyloxy-$C_1$-$C_{10}$-alkyl, —$C_3$-$C_{10}$-alkenyl or —$C_3$-$C_{10}$-alkynyl. Preferred is $C_1$-$C_7$-alkoxy-$C_1$-$C_7$-alkyl, —$C_3$-$C_7$-alkenyl or —$C_3$-$C_7$-alkynyl, or $C_3$-$C_7$-alkenyloxy-$C_1$-$C_7$-alkyl, -$C_3$-$C_7$-alkenyl or —$C_3$-$C_7$-alkynyl.

Substituted NH is, for example, NH which is substituted by $C_1$-$C_8$-alkyl such as methl, ethyl or propyl, phenyl-$C_1$-$C_8$-alkyl such as benzyl or 2-phenethyl, or by acyl, such as $C_2$-$C_8$-alkyl-alkanoyl, phenyl-$C_2$-$C_5$-alkanoyl, benzoyl, $C_1$-$C_8$-alkanesulfonyl or benzenesulfonyl.

An alicyclic residue is, for example, mono-, bi- or polycyclic. Preferred is cycloalkyl and secondarily cycloalkenyl, each of which can also be substituted.

Cycloalkyl in particular $C_3$-$C_8$cycloalkyl. Preferred is cyclopentyl and cyclohexyl.

Cycloalkenyl is in particular $C_3$-$C_7$cycloalkenyl and is preferably cyclopent-2- and -3-enyl, or cyclohex-2- and -3-en-yl.

A heteroalicyclic residue is, for example, an alicyclic residue, wherein at least one carbon atom is replaced by a heteroatom, e.g. NH, substituted NH, O, or S, each of which can also be substituted.

An alicyclic aliphatic residue is, for example, alkyl, alkenyl or alkynyl that is substituted by cycloalkyl or by cycloalkenyl. Preferred is $C_1$-$C_8$-alkyl, $C_2$-$C_8$-alkenyl or $C_2$-$C_8$-alkynyl each of which is substituted by $C_3$-$C_8$-cycloalkyl or by $C_3$-$C_8$-cycloalkenyl, especially cyclopropylmethyl, cyclopentylmethyl, cylohexylmethyl, or cyclohexenyl-methyl.

A heterocyclic aliphatic residue is, for example, $C_1$-$C_8$-alkyl, $C_2$-$C_3$-alkenyl or $C_2$-$C_8$-alkynyl each of which substituted by $C_3$-$C_8$cycloalkyl or by $C_3$-$C_8$-cycloalkenyl wherein one carbon atom of $C_3$-$C_8$cycloalkyl or by $C_3$-$C_8$-cycloalkenyl, respectively, is replaced by NH, substituted NH, O, or S, especially piperidino-methyl or -ethyl.

A carbocyclic aromatic residue is, for example, a mono- or polycyclic (such as bicyclic) or benzoanellated carbocyclic residue, such as phenyl, naphthyl, but also biphenyl, each of which can also be substituted.

A heterocyclic aromatic residue is, for example, 5- or 6-membered and monocyclic radical which has up to four identical or different hetero atoms, such as nitrogen, oxygen or sulfur atoms, preferably one, two, three or four nitrogen atoms, an oxygen atom or a sulfur atom, each of which can also be substituted. Appropriate 5-membered heteroaryl radicals are, for example, monoaza-, diaza-, triaza-, tetraaza-, monooxa- or monothia-cyclic aryl radicals, such as pyrrolyl, pyrazolyl, imidazolyl, triazolyl, tetrazolyl, furyl and thienyl, while suitable appropriate 6-membered radicals are in particular pyridyl.

An araliphatic residue is, for example, $C_1$-$C_8$-alkyl, $C_2$-$C_8$-alkenyl or $C_2$-$C_8$-alkynyl each of which is substituted by phenyl or by naphthyl, especially benzyl, 2-phenethyl or 2-phenyl-ethenyl.

A heteroaraliphatic residue, is for example, $C_1$-$C_8$-alkyl, $C_2$-$C_8$-alkenyl or $C_2$-$C_8$-alkynyl each of which is substituted by pyrazolyl, imidazolyl, triazolyl, tetrazolyl, furyl, thienyl or pyridyl, especially pyridylmethyl.

Alkyl, alkenyl, or alkinyl can also be substituted, for example, by a substituent selected from the group consisting e.g. of an alicyclic residue, a heteroalicyclic residue; a carbocyclic and a heterocyclic aromatic residue; each residue, independently of another, being unsubstituted or substituted by one or more, e.g. two or three, substituents, for example, selected from the group consisting of halogen, amino, substituted amino, mercapto, substituted mercapto, hydroxyl, etherified hydroxyl, carboxy, and amidated carboxy.

Alicyclic or heteroalicyclic residues can also be substituted, for example, by one or more, e.g. two or three, substituents selected from the group consisting e.g. of an aliphatic residue, alicyclic residue, a heteroalicyclic residue; a carbocyclic and a heterocyclic aromatic residue; each residue, independently of another, being unsubstituted or substituted by one or more, e.g. two or three, substituents, for example, selected from the group consisting of halogen; amino, substituted amino, mercapto, substituted mercapto, hydroxyl, etherified hydroxyl, carboxy, and amidated carboxy.

An alicyclic-aliphatic residue, a heteroalicyclic-aliphatic residue, an araliphatic residue or a heteroaraliphatic residue, each residue (e.g. in both the alicyclic and the aliphatic moiety), independently of another, being unsubstituted or substituted by one or more, e.g. two or three, substituents in both structural elements, for example, selected from the group consisting of an aliphatic residue, an alicyclic residue, a heteroalicyclic residue; an alicyclic-aliphatic residue; a heteroalicyclic-aliphatic residue; a carbocyclic aromatic residue, a heterocyclic aromatic residue; an araliphatic residue; an heteroaraliphatic residue, halogen; amino, substituted amino, mercapto, substituted mercapto, hydroxyl, etherified hydroxyl, carboxy, and amidated carboxy.

A carbocyclic or a heterocyclic aromatic residue can also be substituted, for example, by one or more, e.g. two or three, substituents selected from the group consisting e.g. of an aliphatic residue, alicyclic residue, a heteroalicyclic residue; a carbocyclic and a heterocyclic aromatic residue; each residue, independently of another, being unsubstituted or substituted by one or more, e.g. two or three, substituents, for example, selected from the group consisting of halogen; amino, substituted amino, mercapto, substituted mercapto, hydroxyl, etherified hydroxyl, carboxy, and amidated carboxy.

Substituents of an aliphatic residue, an alicyclic residue, a heteroalicyclic residue; an alicyclic-aliphatic residue; a heteroalicyclic-aliphatic residue; a carbocyclic or a heterocyclic aromatic residue; an araliphatic residue or an heteroaraliphatic residue, can likewise be acetalized formyl.

Halogen is in particular halogen of atomic number not more than 53, such as fluorine, chlorine, bromine and iodine.

Substituted mercapto is, for example, substituted by an aliphatic residue, an alicyclic residue, a heteroalicyclic residue; an alicyclic-aliphatic residue; a heteroalicyclic-aliphatic residue; a carbocyclic or a heterocyclic aromatic residue; an araliphatic residue or an heteroaraliphatic residue, each residue, independently of another, being unsubstituted or substituted by one or more, e.g. two or three, substituents, for example, selected from the group consisting of halogen; amino, substituted amino, mercapto, substituted mercapto, hydroxyl, etherified hydroxyl, carboxy, and amidated carboxy.

Etherified hydroxy is, for example, hydroxy etherified by an aliphatic, an alicyclic, heteroalicyclic, an araliphatic, a heteroaryl-aliphatic, a carbocyclic aromatic or heteroaromatic alcohol, each of which can also be substituted.

Esterified carboxy is, for example, carboxy which is esterified by an alcohol which is derived from an aliphatic or araliphatic hydrocarbon radical, such as alkyl, phenyl-alkyl, alkenyl and secondarily alkynyl, and which may be interrupted by —O—, such as alkoxy-alkyl, -alkenyl and -alkynyl. Examples which may be mentioned are $C_1$-$C_7$alkoxy-, phenyl-$C_1$-$C_7$alkoxy-, $C_2$-$C_7$alkenyloxy- and $C_1$-$C_7$alkoxy-$C_1$-$C_7$alkoxy-carbonyl.

Amidated carboxyl is, for example, carbamoyl in which the amino group is unsubstituted or monosubstituted or, independently of one another, disubstituted by an aliphatic or araliphatic hydrocarbon radical or disubstituted by a divalent aliphatic hydrocarbon radical which may be interrupted by O or may be condensed at two adjacent carbon atoms with a benzene ring, in particular alkylene or lower alkyleneoxyalkylene. Examples of appropriately substituted amino groups which may be mentioned are $C_1$-$C_7$alkyl-, $C_2$-$C_7$alkenyl-, $C_2$-$C_7$alkynyl-, phenyl-$C_1$-$C_7$alkyl-, phenyl-$C_2$-$C_7$alkenyl-, phenyl-$C_2$-$C_7$alkynyl-, N—$C_1$-$C_7$alkyl-N-phenyl-$C_1$-$C_7$alkyl- and diphenyl-$C_1$-$C_7$alkylamino and also quinol-1-yl, isoquinol-2-yl, $C_1$-$C_7$alkylene- and $C_1$-$C_7$alkyleneoxy-$C_1$-$C_7$alkylene-amino.

Alkylene is, for example, $C_1$-$C_{10}$alkylene, in particular, $C_1$-$C_7$alkylene, for example methylene, ethylene, or 1,5-pentylene. Corresponding alkylene may also be branched.

Substituted amino has the meanings indicated in connection with substituted carbamoyl and is furthermore acylamino, such as $C_2$-$C_8$-alkanoyl-, phenyl-$C_2$-$C_5$-alkanoyl-, benzoyl-, $C_1$-$C_5$-alkanesulfonyl- or benzenesulfonylamino.

Acetalised formyl is, for example, di-alkoxymethyl or oxyalkyleneoxymethylene. Most preferred is branched oxy-alkylene-oxy-methylene wherein the alkylene group is branched such as oxy-2,3-butylene-oxy-methylene or oxy-2,3-di-methyl-2,3-butylene-oxy-methylene.

Alkanoyl is, for example, $C_2$-$C_{10}$alkanoyl and is in particular $C_2$-$C_7$alkanoyl, such as acetyl, propionyl, butyryl, isobutyryl or pivaloyl. $C_2$-$C_5$alkanoyl is preferred.

Haloalkylsulfamoyl is in particular halo-$C_1$-$C_{10}$alkanesulfamoyl and is in particular $C_2$-$C_7$ alkanesulfamoyl, for example, trifluoromethane-, difluoromethane-, 1,1,2-trifluoroethane- or heptafluoropropanesulfamoyl. Halo-$C_1$-$C_4$alkanesulfamoyl is preferred.

Pyrrolyl is, for example, 2- or 3-pyrrolyl. Pyrazolyl is 3- or 4-pyrazolyl. Imidazolyl is 2- or 4-imidazolyl. Triazolyl is, for example, 1,3,5-1H-triazol-2-yl or 1,3,4-triazol-2-yl. Tetrazolyl is, for example, 1,2,3,4-tetrazol-5-yl, furyl is 2- or 3-furyl and thienyl is 2- or 3-thienyl, while suitable pyridyl is 2-, 3- or 4-pyridyl or corresponding N-oxido-pyridyl.

Alkoxy is, for example, $C_1$-$C_{20}$alkoxy, in particular $C_1$-$C_{10}$alkoxy. Preferred is $C_1$-$C_7$alkoxy, most preferred $C_1$-$C_4$alkoxy such as methoxy, ethoxy, n-propyloxy or tert-butyloxy.

Substituents of residues as mentioned above and below should preferably not comprise those substituents that interfere with the reactants.

Preferred R is selected from the group consisting of phenyl or of pyridyl each of which is unsubstituted or substituted by a substituent selected from the group consisting of halogen, $C_1$-$C_7$alkyl, $C_1$-$C_7$alkoxy, hydroxyl, hydroxyl-$C_1$-$C_7$alkyl, halo-$C_1$-$C_7$alkyl such as $CF_3$, formyl, di-$C_1$-$C_7$alkoxy-methyl, and $C_2$-$C_7$alkylene-methyl; of $C_3$-$C_7$cycloalkyl; of $C_3$-$C_7$cycloalkenyl; of biphenylyl that is unsubstituted or substituted by a substituent selected from the group consisting of halogen, $C_1$-$C_7$alkyl, $C_1$-$C_7$alkoxy, hydroxyl, hydroxyl-$C_1$-$C_7$alkyl, halo-$C_1$-$C_7$alkyl such as $CF_3$, formyl, di-$C_1$-$C_7$alkoxy-methyl, and $C_2$-$C_7$alkylene-methyl, for example 4'-$C_1$-$C_4$alkyl-biphenyl-2-yl, 4'-hydroxy-$C_1$-$C_4$alkyl-biphenyl-2-yl, 4'-halo-$C_1$-$C_4$alkyl-biphenyl-2-yl, 4'-formyl-biphenyl-2yl, 4-di-di-$C_1$-$C_4$alkoxy-methyl, or $C_2$-$C_5$alkylene-methyl; of $C_1$-$C_7$alkyl that is unsubstituted or substituted by a substituent selected from the group consisting of halogen, of phenyl; of phenylsulphonyl, of phenylsuphinyl, and of phenylmercapto, phenyl being in each case unsubstituted or substituted by a substituent selected from the group consisting of halogen, $C_1$-$C_7$alkyl, $C_1$-$C_7$alkoxy, hydroxyl, hydroxyl-$C_1$-$C_7$alkyl, and halo-$C_1$-$C_7$alkyl such as $CF_3$; of carboxy, and of N-phenyl-N—$C_1$-$C_7$alkyl-amino phenyl being in each case unsubstituted or substituted by a substituent selected from the group consisting of halogen, $C_1$-$C_7$alkyl, $C_1$-$C_7$alkoxy, hydroxyl, hydroxyl-$C_1$-$C_7$alkyl, and halo-$C_1$-$C_7$alkyl such as $CF_3$; and of $C_2$-$C_7$alkenyl that is unsubstituted or substituted by a substituent selected from the group consisting of halogen, of phenyl; of carboxy, and of N-phenyl-N—$C_1$-$C_7$alkyl-amino phenyl being in each case unsubstituted or substituted by a substituent selected from the group consisting of halogen, $C_1$-$C_7$alkyl, $C_1$-$C_7$alkoxy, hydroxyl, hydroxyl-$C_1$-$C_7$alkyl, and halo-$C_1$-$C_7$alkyl such as $CF_3$.

Specifically preferred R is selected from the group consisting of halophenyl such as 2-, 4-chlorophenyl, 2-fluorophenyl; of hydroxyphenyl such as 2-hydroxyphenyl; of $CF_3$-phenyl such as 2-$CF_3$-phenyl; of halo-pyridyl such as 2-chloro-5-pyridyl; of hydroxy-pyridyl such as 2-hydroxy-5-pyridyl; of biphenyl that is substituted by $C_1$-$C_4$-alkyl, hydroxyl-$C_1$-$C_4$-alkyl, or formyl; of phenyl-$C_2$-$C_4$-alkenyl; of 1-carboxy-2-phenyl-$C_2$-$C_4$-alkenyl, such as 4'-methyl-biphenyl-2-yl, 4'-bromomethyl-biphenyl-2-yl, 4'-formyl-biphenyl-2-yl, or 4-hydroxymethyl-biphenyl-2-yl; of carboxy-$C_1$-$C_4$-alkyl, for example, carboxy-methyl; of phenylsulphonyl-$C_1$-C-alkyl such as phenylsulphonyl-methyl; of phenylmercapto-$C_1$-$C_4$-alkyl such as phenylmercaptomethyl; of $C_3$-$C_6$-cycloalkyl such as cyclopropyl or cyclobutyl; of $C_3$-$C_6$-cycloalkenyl such as 1-cyclohexenyl; and of N-phenyl-N'—$C_1$-$C_4$-alkyl-amino-$C_1$-$C_4$-alkyl such as 2-(N-phenyl-N'-methyl-amino)-methyl.

The reactions described above and below in the variants are carried out, for example, in the absence or, customarily, in the presence of a suitable solvent or diluent or a mixture thereof, the reaction, as required, being carried out with cooling, at room temperature or with warming, for example, in a temperature range from about −80□C up to the boiling point of the reaction medium, preferably from about −10□ to about +200□C, and, if necessary, in a closed vessel, under pressure, in an inert gas atmosphere and/or under anhydrous conditions.

Preferably, a compound of formula (II a) is used, wherein substituents of variable R do not interfere during the reaction with a compound of formula (II b).

A compound of formula (II a) is preferably a corresponding compound, wherein R is as defined above.

A preferred azide of formula $(R_1)(R_2)M$-$N_3$ (II b) is a corresponding compound, wherein M is aluminium or boron, $R_1$ and $R_2$, independently of one another, is $C_1$-$C_8$-alkyl such as methyl, ethyl, propyl, diisobutyl, tert-butyl or n-octyl; $C_3$-$C_7$alkenyl such as allyl or crotyl, $C_3$-$C_7$-cycloalkyl such as cyclohexyl; phenyl-$C_1$-$C_4$-alkyl such as benzyl or 2-phenethyl; phenyl-$C_3$-$C_5$alkenyl such as cinnamyl, or $C_3$-$C_8$-cycloalkyl-$C_1$-$C_8$alkyl such as cyclopropylmethyl or cyclohexylmethyl. Likewise, $R_1$ and $R_2$, independently of one another, is phenyl-$C_2$-$C_5$alkenyl.

Especially preferred azides are those as mentioned in the Examples.

The molar ratio of an azide of formula (II b) and a nitrile of formula (II a) is in a range from 5 to 1, preferably, from 3 to 1, most preferably, from 1,8 to 1 or from 1,2 to 1.

An inert solvent, diluent or mixture thereof should be selected which means that it cannot react with the starting material or intermediates. A suitable solvent is, for example, selected from the group consisting of aliphatic, cycloaliphatic and aromatic hydrocarbon, such as an $C_5$-$C_{10}$-alkane e.g. heptane, a cycloalkane such as cyclohexane; and alkylated $C_3$-$C_7$cycloalkane such as methyl-cyclohexane or 1,3-dimethyl-cyclohexane, an alkylated benzene such as ethylbenzene, toluene, xylene, cumene, or mesitylene; a halogenated aromatic solvent such as chlorobenzene, o-, m- or p-chlorotoluene, dichlorobenzene, and trifluoromethylbenzene which may be further substituted e.g. by $C_1$-$C_7$alkyl or $C_1$-$C_7$alkoxy; and a halogenated hydrocarbon, for example, a halogenated aromatic compound, such as chlorobenzene. A further solvent may be an ether, such as tetrahydrofurane. Furthermore, a suitable solvent, diluent or mixture thereof should have a boiling point that is high enough to be used under the reaction conditions.

Preferred solvents or diluents are aliphatic hydrocarbons, for example, $C_6$-$C_9$alkanes such as heptane or n-octane; aromatic hydrocarbons, for example, phenyl substituted by $C_1$-$C_4$alkyl such as toluene or xylene, or mixtures thereof.

The reaction temperature is preferred in the temperature range of from room temperature to the boiling point of the solvent, diluent or mixture thereof, for example, a reaction temperature range is from about 20° C. to about 170° C., preferably, from about 60° C. to about 130° C. or to about 140° C., depending on the reactivity and combination of the reactants. A person skilled in the art is fully enabled to select corresponding suitable solvent and diluent systems and reaction conditions adapted to the choice of the solvent system and reactants.

The reaction is most preferably carried out under anhydrous conditions.

In a preferred embodiment of the present invention, the invention is carried out in a temperature range of from 80° C. to 120° C., preferably between 90° C. and 110° C.

The isolation step is carried out according to conventional isolation methods, such as by crystallizing the resulting compound of formula (I), (IV), (IV c), (V), (VI), (VII), or (VII'), respectively, or a tautomer or salt thereof, from the reaction mixture or by chromatography of the reaction mixture, such as by crystallizing the resulting compound from the reaction mixture—if desired or necessary after work-up, especially by extraction—or by chromatography of the reaction mixture. Reference in this context is also made to the working examples.

Compounds of formula (II a) are either known or can be prepared using methods known in the art.

Preferred are compounds of formula (II a), wherein R represents a carbocyclic or heterocyclic residues.

The present invention likewise relates to a compound of formula (II b). Preferred compounds of formula (II b) are those, wherein $R_1$ and $R_2$, independently of one another, are $C_1$-$C_{10}$alkyl, $C_3$-$C_8$alkenyl, $C_3$-$C_8$-cycloalkyl, alkylated $C_3$-$C_8$-cycloalkyl or ar-$C_1$-$C_5$alkyl, especially methyl, ethyl, isopropyl, butyl, isobutyl, octyl, allyl, cyclopropyl, cyclopentyl, cyclohexyl, methyl-cyclohexyl, or benzyl.

Azides of formula (II b) can be prepared, for example, by reacting a compound of formula $(R_1)(R_2)M-X$ (II c), wherein M is aluminium or boron, $R_1$ and $R_2$ have the meanings as defined above and X is a leaving group e.g. halogen, such as fluoride, chloride, bromide or iodide; or a sulphonate, such as an alkane sulfonate e.g. methanesulphonate; a halogenated alkane sulfonate e.g. trifluoromethansulfonate, an aromatic sulphonate e.g. tosylate; with an azide, preferably an alkaline metal azide, such as a lithium, sodium or potassium azide.

The formation of an azide of formula (II b) is carried out, in particular, in the presence of an inert solvent or diluent or a mixture thereof, in a temperature range of 0° C. to 120° C. The reaction is most preferably carried out under anhydrous conditions.

Preferred azides comprise compounds of formula (II b), wherein $R_1$ and $R_2$, independently of one another, represent $C_1$-$C_8$-alkyl such as ethyl, iso-propyl, n-propyl, n-butyl, sec-butyl, tert-butyl or n-octyl, $C_3$-$C_8$-cycloalkyl, $C_3$-$C_8$-cycloalkyl-$C_1$-$C_8$-alkyl or aryl-$C_1$-$C_8$-alkyl such as benzyl or 2 phenethyl; and M is boron or aluminium. Corresponding representatives are dimethyl aluminium azide, diethyl aluminium azide, diisopropyl aluminium azide, dipropyl aluminium azide, diisobutyl aluminium azide, dibutyl aluminium azide, dicyclohexyl aluminium azide, diethyl boron azide, diisopropyl boron azide, dipropyl boron azide, diisobutyl boron azide, dibutyl boron azide or dicyclohexyl boron azide, furthermore diaryl boron azide such as diphenyl boron azide.

It might be that, dependent on the kind of substituents, reactive substituents could also react with the azide. For example, an aromatic hydroxy group or a benzylic hydroxyl group may react with an azide of formula (II b), however, the resulting hydroxy function masked by a metal or by an organo metal group can be split with e.g. an acid resulting in a compound of formula (I); accordingly, in this situation, a higher amount of a compound of formula (II a) needs to be used. An ester group might form an acyl-azide with a compound of formula (II b), while an epoxy ring structure might be opened with a compound of formula (II b). However, the person skilled in the art would be able to either directly anticipate that starting compounds with specific reactive substituents could not be used, as these substituents might react with the azide instead of the cyano function, or the person skilled in the art would, when corresponding side reactions are realized, protect corresponding reactive groups and later on split-off the corresponding protecting groups by using conventional methods known per se.

The process of the present invention likewise comprises protecting reactive substituents of compounds of formulae (II a) and (II b) and, after formation of the tetrazole ring, splitting-off the corresponding protective group(s), especially by using conventional methods known per se e.g. by the person skilled in the pertinent art who is familiar with protecting and de-protecting functional groups.

In a preferred embodiment of the present invention, before the reaction of a compound of formula (II a) with a compound of formula (II b), a compound of formula (II a) wherein R comprises a reactive group that can be protected against the reagent of formula (II b) can be protected. Then a resulting protected compound is reacted as described herein with a compound of formula (II b) and from a resulting compound the protecting groups is split off resulting in a compound of formula (I) or a tautomere thereof. This principle can likewise be applied to the manufacture of a compound of formulae (IV), (V), (VI), respectively.

In a preferred embodiment of this variant, OH groups, such as aromatic e.g. phenolic or benzylic OH groups, can be either masked or protected, respectively. A corresponding OH group can be masked, for example, by treatment with a compound of formula (II d) $M'(R_3)_n$ wherein M' represents a suitable element of groups 1a, 2a, 3a, and 4 of the Periodic Table of Elements, especially an element selected from the group consisting of Li, Na, K, Mg, Ca, B, Al, and Si; $R_3$, independently of one another, is hydrogen, a leaving group such as halogen e.g. chlorine or bromine, $NH_2$, alkyl such as $C_1$-$C_8$-alkyl, cycloalkyl such as $C_3$-$C_7$-cycloalkyl e.g. cyclopropyl or cyclohexyl, carbocyclic aryl such as phenyl or substituted phenyl, carbocyclic aryl-alkyl such as phenyl-$C_1$-$C_4$- alkyl e.g. benzyl or 1- or 2-phenethyl, $C_1$-$C_8$-alkoxy such as methoxy, ethoxy, isopropyloxy, tert-butyloxy, n-octyloxy, and the index "n" corresponds to the valence of the element M'. $R_3$ can only represent one leaving group such as halogen.

A preferred compound of formula (II d) comprises corresponding alkaline metal hydride or amide such as NaH, KH, $NaNH_2$, $KNH_2$; $CaH_2$ and $MgH_2$, a corresponding alkaline metal organyl, for example, M'-$C_1$-$C_8$-alkyl such as isobutyl-Li, butyl-Li, isobutyl-Li, tert-butyl-Li, n-hexyl-Li, n-hexyl-Li.

A preferred compound of formula (II d) comprises a corresponding alkaline metal alcoholate such as sodium or potassium $C_1$-$C_5$-alkanolate.

A preferred compound of formula (II d) comprises a corresponding $C_1$-$C_8$-alkyl, $C_3$-$C_7$-cycloalkyl, phenyl or substituted phenyl organyl formed with B or Al such as trimethyl-Al, triethyl-Al, or a corresponding $C_1$-$C_8$-alkoxy organyl formed with B or Al such as trimethoxy-B, triethoxy-B, tri-isoproyloxy-B, tri-butyloxy-B and tri-n-butyloxy-B. A preferred compound of formula (II d) comprises a corresponding halide of $C_1$-$C_8$-alkyl, phenyl-$C_1$-$C_4$-alkyl, $C_3$-$C_7$-cycloalkyl, phenyl or substituted phenyl organyl formed with Si such as trimethyl-Si-chloride, triethyl-Si-chloride, tribenzyl-Si-chloride, tert-buty-diphenyl-B-chloride, and triphenyl-Si-chloride. Most preferred is LiH, but also trimethyl-Al and triethyl-Al.

A reactive group of a compound of formula (II a), for example, a corresponding OH group, can also be protected, for example, by a suitable OH protecting group.

Most angiotensin II receptor antagonists have two essential structural elements, the so-called "core part" and the "pharmacophore element".

Examples for corresponding angiotensin II receptor antagonists can be taken from following table:

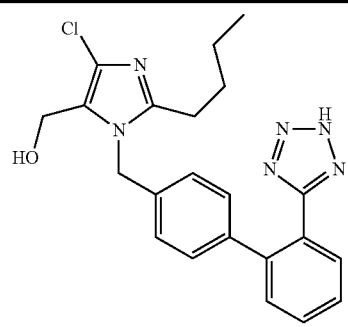

Losartan (MSD)

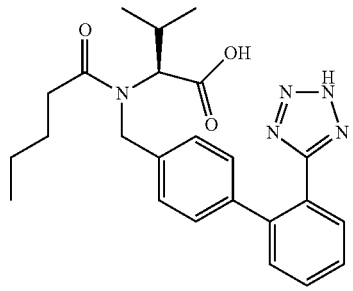

Valsartan (Novartis)

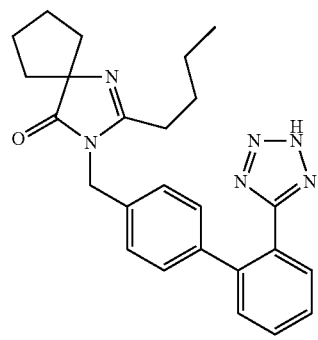

Irbesartan
(Sanofi, BMS)

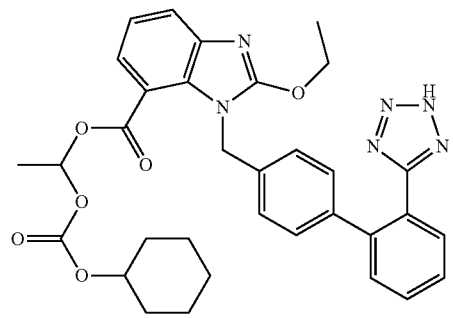

Candesartan-Cilexetil (Takeda)

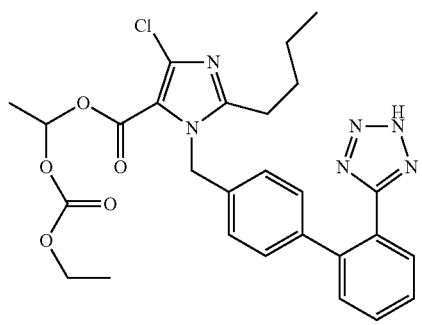

Elisartan
(Hafslund, Nycomed)

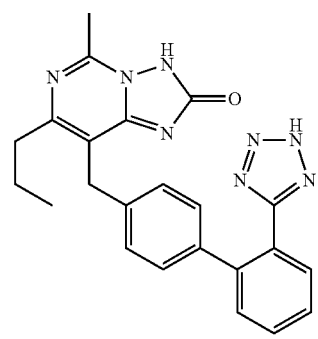

Ripisartan (BMS)

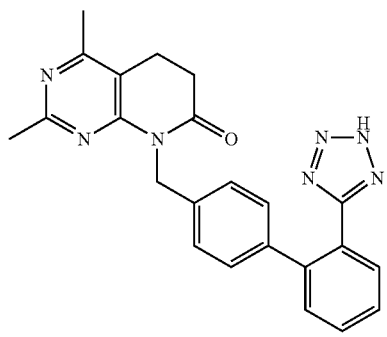
Tasosartan
(Wyeth-Ayerst)
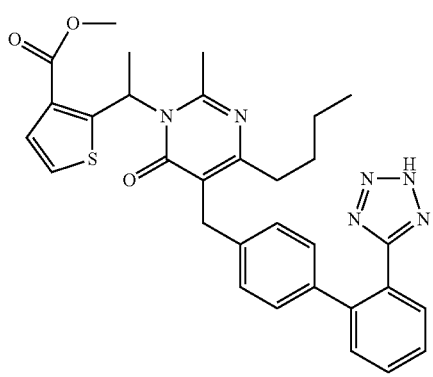
Milfasartan
(Lusofarmaco, Menarini)
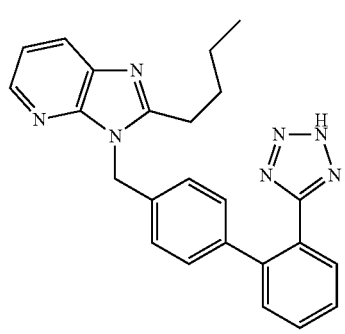
FK-739 (Fujisawa)
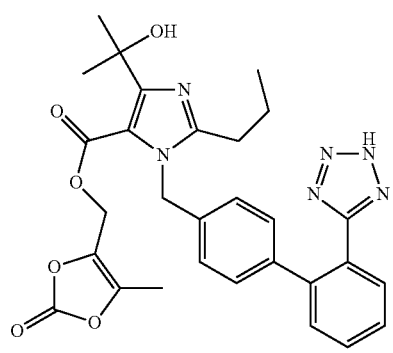
Olmesartan
(Sankyo, Recordati)
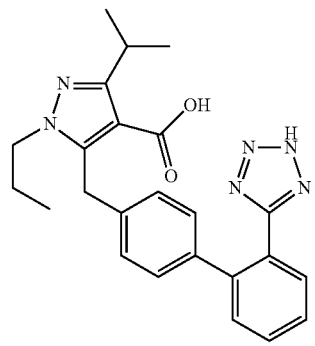
UR-7247 (Uriach)
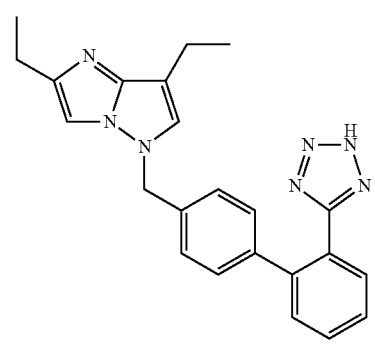
YM-358 (Yamanouchi)
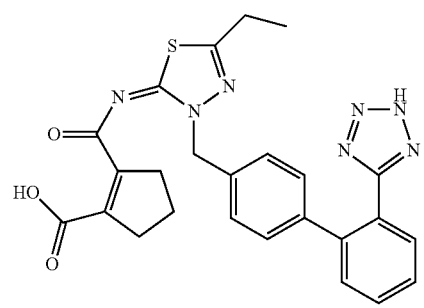
KRH-94 (Kissei)
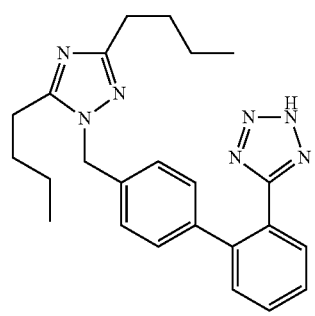
SC-52458 (Searle)
The core part of angiotensin II receptor antagonists comprises e.g. core elements derived from above table, for example, following structural elements:

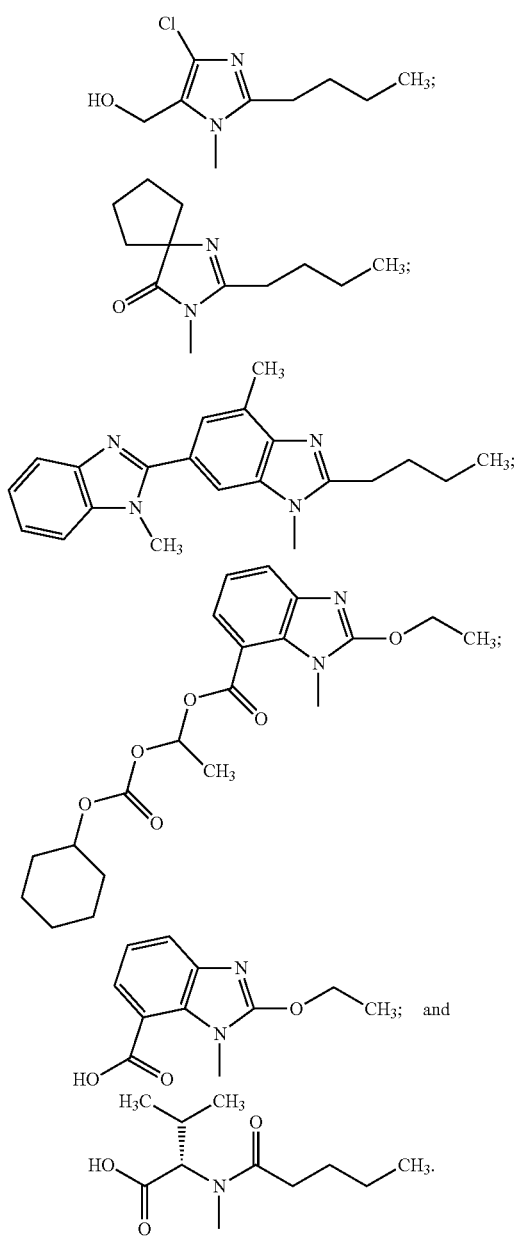

A further preferred core part of an angiotensin II receptor antagonist has following structure:

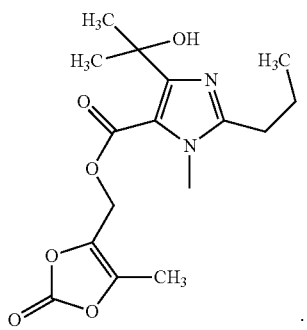 [SMILES: CCCc1nc(C(C)(C)O)c(C(=O)OCc2oc(=O)oc2C)n1C]

The pharmacophore element of corresponding angiotensin II receptor antagonists is represented by formula (IIIa)

or is a tautomeric form thereof.

A tautomeric form of the side chain of formula (III a) is represented by formula (III b)

(IIIb)

The present invention likewise relates to a process for the manufacture of said angiotensin II receptor antagonists having as structural feature side the chain of formula (III a) is represented by formula (IIIa)

or a tautomeric form thereof, especially of angiotensin II receptor antagonists as shown in above table.

The present invention likewise relates to a process for the manufacture of said angiotensin II receptor antagonists having as structural feature a tetrazol ring, e.g. of formula (IV), (IV)

or a tautomeric form thereof, wherein Rx represents a structural element selected from the group consisting of

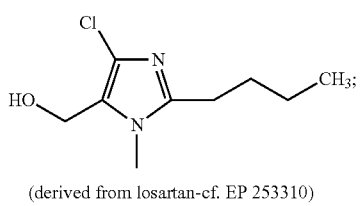

(derived from losartan-cf. EP 253310)

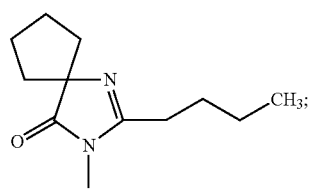

(derived from irbesartan-cf. EP 454511)

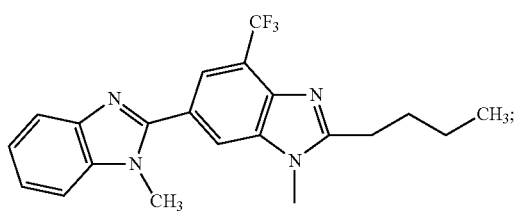

(derived from UR-7247)

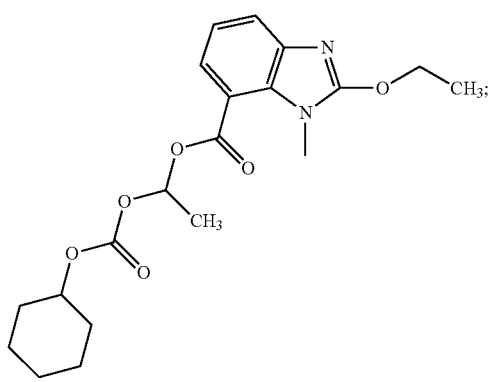

(derived from candesartan-cilexetril-EP 459136)

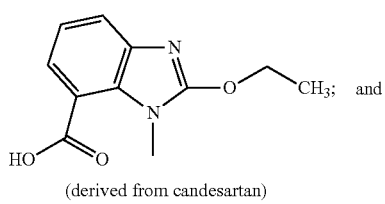

(derived from candesartan)

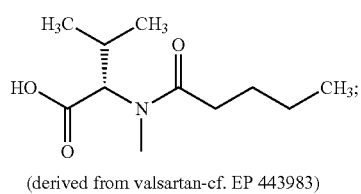

(derived from valsartan-cf. EP 443983)

-continued

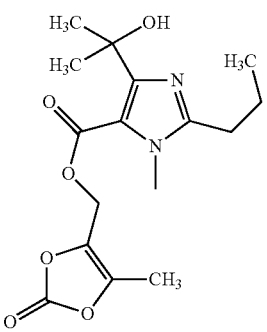

(derived from olmesartan)

or, in each case, a salt thereof.

This process is characterized by reacting a compound of formula (IV a)

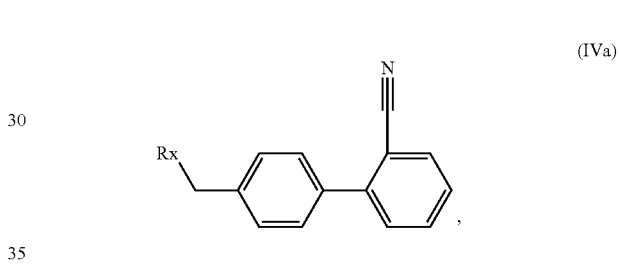

(IVa)

wherein Rx has the meanings as given above, with a compound of formula $(R_1)(R_2)M$-$N_3$ (II b), wherein $R_1$ and $R_2$, independently of one another, represent an organic residue; and isolating the resulting compound of formula (IV).

A preferred angiotensin II receptor antagonist is the compound of formula

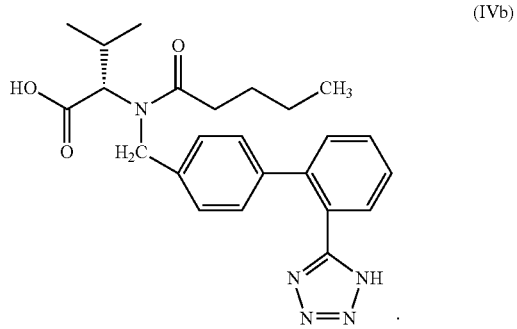 [SMILES: CCCCC(=O)N(Cc1ccc(-c2ccccc2-c2nnn[nH]2)cc1)[C@H](C(=O)O)C(C)C]

(IVb)

A preferred variant of the process according to the present invention for the manufacture of a compound of formula (IV b) is characterized by reacting a compound of formula (IV c)

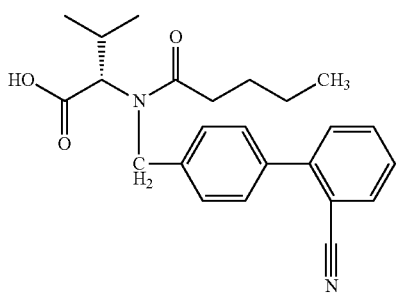
(IVc)

or an ester thereof with an azide of formula $(R_1)(R_2)M-N_3$ (IIb), wherein $R_1$ and $R_2$, independently of each other, have the meanings as defined above, and isolating the compound of formula (IV b).

An ester of a compound of formula (IV c) is, for example, an ester derived from an aliphatic, araliphatic, cycloaliphatic, cycloaliphatic-aliphatic or aromatic alcohol. Preferred is a $C_1$-$C_7$-alkyl ester or a aryl-$C_1$-$C_2$-alkyl ester, most preferred a benzylester thereof.

A preferred embodiment of the present invention is a process for the manufacture of a compound of formula

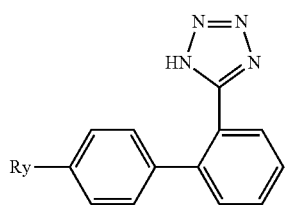
(V)

a tautomeric form thereof wherein Ry represents $C_1$-$C_8$-alkyl such as methyl; $C_1$-$C_8$-alkyl substituted by X' and X' being halogen, sulphonyloxy, hydroxyl, protected hydroxyl, such as bromomethyl, or an acetal of formyl; and $X_1$ being in a benzylic position, comprising reacting a compound of formula (IV a)

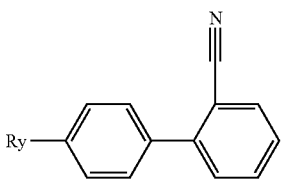
(Va)

with a compound of formula $(R_1)(R_2)M-N_3$ (II b), wherein $R_1$ and $R_2$, independently of one another, represent an organic residue; and isolating the resulting compound of formula (V).

An acetal of a formyl group is, for example, the corresponding di-$C_1$-$C_8$alkoxymethyl such as dimethoxy- or diethoxy-methyl, or methylene-oxy-$C_2$-$C_6$-alkylene-oxy such as methyleneoxy-ethyleneoxy.

The present invention likewise relates to the above reaction. Furthermore, the present invention relates to the compounds of formula (VI) or a tautomer or a salt thereof in a form being completely free of tin. The present invention also relates to compounds of formula (VI) whenever obtained according to above reaction.

A variant of the process for the manufacture of the compound of formula (V) is a process for the manufacture of a compound of formula (VI)

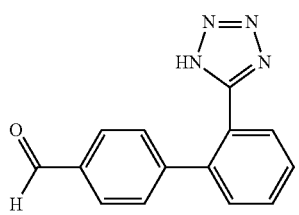
(VI)

or a tautomer or salt thereof, comprising
(a) treating a compound of formula (VI a)

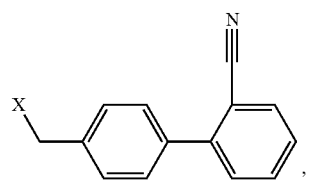
(VIa)

wherein X represents a leaving group, first with a nucleophilic agent and then with a "solvolytic" base resulting in a compound of formula (VI b)

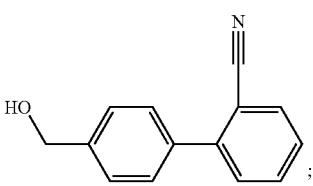
(VIb)

(b) reacting a compound of formula (V b) with an azide of formula $(R_1)(R_2)M-N_3$ (II b), wherein the variables $R_1$ and $R_2$, independently of one another, have the meanings as defined above: resultina in a compound of formula (VI c)

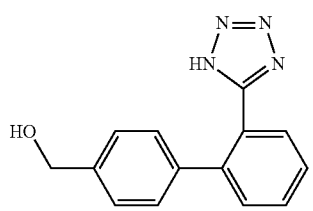
(VIc)

or a tautomer or salt thereof
(c) oxidizing a compound of formula (VI c) or a tautomer or salt thereof resulting in a compound of formula (VI)

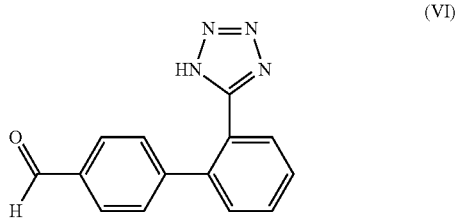 [SMILES: O=Cc1ccc(-c2ccccc2-c2nnn[nH]2)cc1]

(VI)

or a tautomer or salt thereof; and
(d) isolating the compound of formula (VI) or a tautomer or salt thereof.

Accordingly, variable R comprises the meanings of variables Rx, Ry and also represents formyl.

The present invention relates to each of reaction steps (a) to (c) and to the product obtained according to the complete reaction sequence, but also according to each of reaction steps (a) to (c).

The reactions described above and below in the variants are carried out in a manner known per se, for example in the absence or, customarily, in the presence of a suitable solvent or diluent or a mixture thereof, the reaction, as required, being carried out with cooling, at room temperature or with warming, for example in a temperature range from about −80°C up to the boiling point of the reaction medium, preferably from about −10° to about +200°C, and, if necessary, in a closed vessel, under pressure, in an inert gas atmosphere and/or under anhydrous conditions.

Step (a) is carried out, for example, in the presence of a base, e.g. first a nucleophilic agent followed by treatment with a saponifying base.

A suitable nucleophilic agent is, for example, an alkaline metal salt of a $C_2$-$C_{10}$-alkanecarboxylic acid, especially of a $C_2$-$C_5$-alkanecarboxylic acid, an araliphatic carboxylcic acid or an aromatic carboxylic acid, or aliphatic ammonium acetates, especially tetra-$C_1$-$C_7$-alkyl-ammonium acetates. Examples comprise e.g. lithium acetate, sodium acetate, potassium acetate, and tetraethylammonium acetate.

Suitable saponifying bases are, for example, alkali metal hydroxides, hydrides, amides, alkanolates, carbonates, or lower alkylsilylamides, naphthaleneamines, lower alkylamines, basic heterocycles, ammonium hydroxides, and carbocyclic amines. Examples which may be mentioned are sodium hydroxide, sodium hydride, sodium amide, sodium methoxide, sodium ethoxide, potassium tert-butoxide, potassium carbonate, benzyltrimethylammonium hydroxide, 1,5-diazabicyclo[4.3.0]non-5-ene (DBN) and 1,8-diaza-bicyclo[5.4.0]undec-7-ene (DBU), the last two bases preferably in the presence of water.

Suitable saponifying bases are preferably used in the presence of water. At least stochiometric amounts of water is used, especially a molar access of water is preferred.

Likewise, in a specially preferred embodiment Step (a) is carried out in the presence of a phase transfer catalyst, for example, those known in the art. Suitable phase transfer catalysts comprise tri-$C_1$-$C_5$-alkyl-ar-$C_1$-$C_5$alkyl-ammonium halides such as corresponding chlorides or bromides, tetra-$C_1$-$C_5$-alkyl-ammonium halides such as corresponding chlorides or bromides, di-$C_1$-$C_8$-alkyl-diar-$C_1$-$C_5$alkyl-ammonium halides such as corresponding chlorides or bromides. Examples are tetrabutyl ammonium bromide or triethylbenzylammonium chloride.

More than one mol equivalent of a base is normally used, preferably from 1.1 to 1.5 equivalents.

An inert solvent or a mixture of solvents is used. Suitable solvents comprise e.g. hydrocarbons such as heptane, octane, toluene or xylene, a halogenated hydrocarbons such as methylenechloride, 1,2-dichloroethane, chlorobenzene, fluorobenzene or trifluorobenzene.

The reaction temperature is, for example, from 0° C. to the boiling point of the solvent, preferably from 0° C. to 130° C., more preferably from 40° C. to 80° C.

The present invention relates to the reaction Step (a). This reaction step comprises two separate steps and it is suprising that the yield is nearly quantitative (>99% by weight theory). The present invention also relates to compounds of formula (VI b) whenever obtained according to process Step (a).

Step (b): The molar ratio of an azide of formula (II b) and a nitrile of formula (VI b) is in a range from 5 to 1, preferably, from 3 to 1, most preferably, from 1,8 to 1 or from 1,2 to 1.

An inert solvent, diluent or mixture thereof should be selected which means that it cannot react with the starting material or intermediates. A suitable solvent is, for example, selected from the group consisting of aliphatic, cycloaliphatic and aromatic hydrocarbon, such as an $C_5$-$C_{10}$-alkane e.g. heptane, a cycloalkane such as cyclohexane; an alkylated $C_3$-$C_7$cycloalkane such as methyl-cyclohexane or 1,3-dimethyl-cyclohexane, an alkylated benzene such as ethylbenzene, toluene, xylene, cumene, or mesitylene; a halogenated aromatic solvent such as chlorobenzene, chlorotoluene, dichlorobenzene, and trifluoromethylbenzene; a halogenated hydrocarbon, for example, a halogenated aromatic compound, such as chlorobenzene. Furthermore, a suitable solvent, diluent or mixture thereof should have a boiling point that is high enough to be used under the reaction conditions.

Preferred solvents or diluents are aliphatic hydrocarbons, for example, $C_6$-$C_9$alkanes such as heptane; aromatic hydrocarbons, for example, phenyl substituted by $C_1$-$C_4$alkyl such as toluene or xylene, or mixtures thereof.

The reaction temperature is preferred in the temperature range of from room temperature to the boiling point of the solvent, diluent or mixture thereof, for example, a reaction temperature range is from about 20° C. to about 170° C., preferably, from about 60° C. to about 130° C., depending on the reactivity and combination of the reactants. A person skilled in the art is fully enabled to select corresponding suitable solvent and diluent systems and reaction conditions adapted to the choice of the solvent system and reactants.

The reaction is most preferably carried out under anhydrous conditions.

In a preferred embodiment of the present invention, the invention is carried out in a temperature range of from 80 to 120° C., preferably between 90 and 110° C.

The present invention likewise relates to reaction Step (b). Furthermore, the present invention relates to the compounds of formula (VI c) or a tautomer or a salt thereof in a form being completely free of tin. The present invention also relates to compounds of formula (VI c) whenever obtained according to process Step (b).

Step (c): The oxidation is carried out in the presence of a suitable oxidizing agent. A suitable oxidizing agent is for example, an alkali metal hypochlorite such as lithium or sodium or potassium hypochlorite, calcium hypochlorite, "a Tempo" or an analogue (cf. Fluka) thereof or an oxidizing agent selected from the group consisting of $HNO_2$, $HNO_3$ or corresponding anhydrides thereof, and peroxodisulfates.

When using e.g. an alkali metal hypochlorite as oxidizing agent, the oxidation is carried out, for example, in an inert solvent, e.g. a solvent that is inert against oxidation, such as a lower alkanecarboxylic acid, for example acetic acid, a heterocyclic aromatic, for example pyridine, a halogenated hydrocarbon, alkane nitrile, for example, acetonitrile, or water or a mixture thereof, if necessary with cooling or warming, for example from about 0□ to about 50□C, for example, at room temperature. In a preferred variant, the reaction is carried out in an aqueous medium and in the presence of a base. A suitable base is, among others, an alkaline carbonate, such as potassium carbonate.

When using oxidizing agents such as $HNO_2$, $HNO_3$ or corresponding anhydrides thereof, or peroxodisulfates, especially nitric acid, in a preferred variant an alkylated aromatic hydrocarbon such as toluene or xylene may be used as solvent. In a preferred variant of the oxidization with as $HNO_2$, $HNO_3$ or corresponding anhydrides thereof, or peroxodisulfates, the reaction is preferably carried out in a temperature range from about 0° C. to room temperature or to 60° C. Surprisingly, no oxidation of the solvent is observed; i.e. the methyl groups in toluene or xylene are resistant to oxidation. Accordingly, the use of oxidizing agents such as $HNO_2$, $HNO_3$ or corresponding anhydrides thereof, or peroxodisulfates is likewise a subject matter of the present invention as is reaction Step c), especially when using as oxidizing agents such as $HNO_2$, $HNO_3$ or corresponding anhydrides thereof, or peroxodisulfates in the an alkylated aromatic hydrocarbon solvent, especially in toluene and xylene. In another preferred variant, $HNO_3$ is used in water free form or in an aqueous solution from about 40% to about 95%, preferably from 40 to 65%.

The use of oxidizing agents such as $HNO_2$, $HNO_3$ or corresponding anhydrides thereof, or peroxodisulfates, especially nitric acid, provides surprising results. For example, the corresponding oxidization to an aldehyde is effected without further oxidizing the aldehyde function to the carboxy group. Accordingly, the use of said oxidizing agents is likewise a subject matter of the present invention.

The present invention also relates to compounds of formula (VI) whenever obtained according to process Step (c).

Step (d): The isolation step of a compound of formula (VI) is carried out according to conventional isolation methods, such as by crystallizing the resulting compound of formula (VI) from the reaction mixture—if desired or necessary after work-up, especially by extraction—or by chromatography of the reaction mixture.

A further preferred embodiment of the present invention is a process for the manufacture of a compound of formula

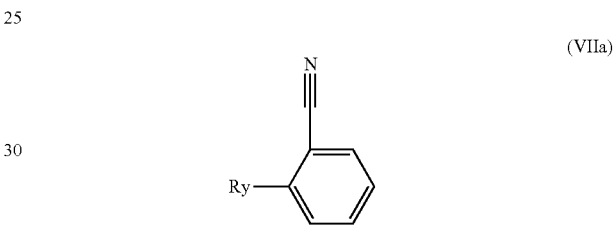

a tautomeric form thereof, wherein Ry represents $C_1$-$C_8$-alkyl such as methyl; $C_1$-$C_8$-alkyl substituted by X' and X' being halogen, sulphonyloxy, hydroxyl, protected hydroxyl, such as bromomethyl, or an acetal of formyl; comprising reacting a compound of formula (VII a')

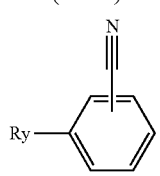

with a compound of formula $(R_1)(R_2)M$-$N_3$ (II b), wherein $R_1$ and $R_2$, independently of one another, represent an organic residue; and isolating the resulting compound of formula (VII').

A further preferred embodiment of the present invention is a process for the manufacture of a compound of formula

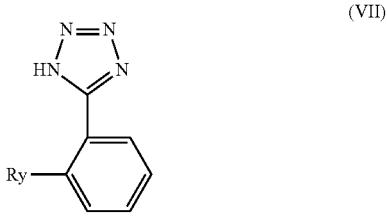

a tautomeric form thereof, wherein Ry represents $C_1$-$C_8$-alkyl such as methyl; $C_1$-$C_8$-alkyl substituted by X' and X' being halogen, sulphonyloxy, hydroxyl, protected hydroxyl, such as bromomethyl, formyl or an acetal thereof; comprising reacting a compound of formula (VII a)

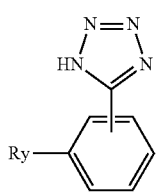

with a compound of formula $(R_1)(R_2)M$-$N_3$ (II b), wherein $R_1$ and $R_2$, independently of one another, represent an organic residue; and isolating the resulting compound of formula (VII).

The present invention likewise relates to the above reaction. Furthermore, the present invention relates to the compounds of formula (VII) or a tautomer or a salt thereof in a form being completely free of tin. The present invention also relates to compounds of formula (VII) whenever obtained according to above reaction.

The isolation step of a compound of formulae (VI) or (VII) or (VII'), respectively, is carried out according to conventional isolation methods, such as by crystallizing the resulting compound of formula (VI)) or (VII), respectively, from the reaction mixture or by chromatography of the reaction mixture.

The conversion of an acid into a salt is carried out in a manner known per se. Thus, for example, a salt with a base is obtained by treating the acid form with a base. Salts with a base can, on the other hand, be converted into the acid (free compound) in a customary manner, and salts with a base can be converted, for example, by treating with a suitable acid agent.

The present invention likewise relates to a compound of formulae (I), (IV), (IV b), (V), (VI), (VII), (VII') or a tautomer or salt thereof in a form being completely free of tin.

The present invention likewise relates to the use of a compound of formula (II b) in a process for the manufacture of a compound of formulae (I), (IV), (IV b), (V), (VI), (VII), (VII') or a tautomer or salt thereof, especially in a form being completely free of tin.

The invention relates to the compounds obtained according any process of the present invention.

The examples outline specific embodiments of the present invention, but are not to limit the scope of the invention.

EXAMPLE 1

5-(2-Chlorophenyl)-1H-tetrazole

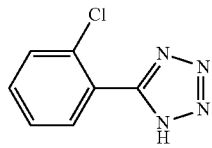

20 mmol (1.3 g) of sodium azide are charged to a 25 ml flask under argon atmosphere followed by slow addition (via syringe) of 11 ml of a solution of diethyl aluminium chloride (1.8 molar in toluene), 20 mmol, at 0° C. under stirring. The suspension is stirred over night at room temperature. Then 2.06 g (15 mmol) solid 2-chloro-benzonitrile are added and the mixture is heated at external temperature of 90° C. for 9 hours. After this time the conversion was 91.5% (HPLC). For complete conversion (>99.5%, HPLC) the reaction mixture is kept for additional 6 hours at 90° C. For work up the reaction mixture was quenched at 0° C. under stirring on 20 ml HCl (6N) which contains 2.6 g of NaNO₂ to destroy excess hydrazoic acid. The thick white precipitate which is formed (product) is stirred at 0° C. for additional 1 hour and then filtered and dried over night at 50° C. to give the white crystalline product.

m.p. 173-175° C.

Tlc: $R_f$-value: 0.48, toluene:EtOAc:AcOH (20:20:1); SiO₂-plates.

EXAMPLE 2

5-(2-Hydroxyphenyl)-1H-tetrazole

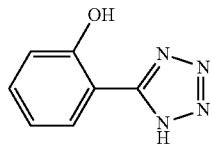 [SMILES: Oc1ccccc1-c1nnn[nH]1]

Method A:

286 mg of granular sodium azide (4.4 mmol) are added to a cold solution of diethyl aluminium chloride (4.4 mmol, 1M in toluene) and the mixture is stirred at room temperature for 4 hours (h).

A solution of 2-hydroxybenzonitrile (4 mmol, 476 mg) in 3 ml of toluene, cooled at 0° C., is treated with 2.2 ml of triethyl aluminium (4 mmol, 1.8 M in toluene). The mixture reaction is warmed to room temperature and stirred for 1 hour. The mixture is cooled to 0° C., treated with the solution of diethyl aluminium azide, gradually warmed to 85° C. and stirred over two days. The reaction mixture is cooled to −10° C. and treated drop wise with 7 ml of HCl 6 N. 10 ml of ethyl acetate are added and the mixture is extracted once with 10 ml of water, once with 10 ml of NaCl saturated. The combined aqueous layers are extracted three times with 10 ml of ethyl acetate. The combined organic phases are dried over Na₂SO₄. The solvent is removed to give the crude product.

Method B:

260 mg of granular sodium azide (4 mmol) is added to a cold solution of diethyl aluminium chloride (4 mmol, 1.8 M in toluene) diluted with 10 ml of toluene, and the mixture is stirred at room temperature for 4 hours. The stirred solution is cooled at 0° C. and 238 mg of 2-hydroxybenzonitrile (2 mmol) are added. The reaction mixture is warmed to 80° C. and stirred over night. After 20 hours the conversions was 83%. Then the temperature is increased to 100° C. and stirred 12 hours. At a conversion of around 90% the reaction is worked up. The reaction mixture is cooled to 0° C. and treated drop wise with 7 ml of HCl 6 M, 5 ml of water, 10 ml of ethyl acetate, 8 ml of saturated NaCl (sat.) and extracted. The organic phase is reextracted twice with 20 ml of water. The combined aqueous layers are extracted twice with 20 ml of ethyl acetate. The combining organic phases are dried over Na₂SO₄. The solvent is removed to give the crude product. The crude product is crystallized from ethyl acetate to give the pure product.

m.p.: 220-222° C.,

Tlc: Rf-value: 0.46, toluene:EtOAc:AcOH (20:20:1).

HPLC:

Hewlett Packard, solvents. H₃PO4, acetonitrile/water; flow: 2 ml/min; injection: 5.0 µl; wavelength 220 nm, 40° C. Column: Merck, Chromolith Performance, RP-18e 100-4.6 mm; Ret. Time: 4.12 min.

EXAMPLE 3a 5-(4'-methylbiphenyl-2-yl)-1H-tetrazole

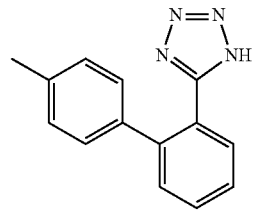 [SMILES: Cc1ccc(-c2ccccc2-c2nnn[nH]2)cc1]

A 20 ml flask is dried under argon and then charged with 7 ml of diisobutylaluminium fluoride (1 molar in hexane) followed by 5 ml of toluene and 455 mg of NaN₃ (7 mmol). After stirring the suspension for 4 hours at room temperature 966 mg of solid ortho-tolylbenzonitrile (OTBN) is added at 0° C. in one portion. The suspension is warmed up to 130° C. (ext. temp.) with an internal temperature of 100° C. After 44 h at 130° C. (ext. temp.) the conversion is >93%. The reaction mixture was quenched in hydrochloric acid (6 molar). After addition of 10 ml of toluene the layers are separated, the organic layer is washed twice with 20 ml of water, dried over sodium sulfate and evaporated to give a crystalline residue of the product.

Physicochemical data see example 3b.

Beispiel 1

EXAMPLE 3b 5-(4'-methylbiphenyl-2-yl)-1H-tetrazole

Same reaction as in example 3a was carried out, but with diethylaluminium azide at higher concentration and higher temperatur:

Under similar conditions with diethylaluminium azide (prepared from diethylaluminium chloride and $NaN_3$) in toluene and OTBN a conversion of 98.5% was obtained after 40 hours at internal temperature of ca. 110° C. (reflux), external temperatur 135° C.

A dry 50 ml flask is charged with 5 ml toluene and 1.3 g (20 mmol) of dry solid sodium azide. The stirred suspension is cooled to 0° C. and 11 ml of a 1.8 molar solution of diethylaluminium chloride (20 mmol) is added via syringe during 10 minutes. The suspension is stirred for 4 to 6 hours or over night at room temperature. Then the suspension is cooled to 0° C. and a solution of o-tolylbenzonitrile (2.1 g, 11 mmol) in 5 ml toluene is added dropwise during 5 minutes. The stirred suspensiun is heated up to reflux and after 7 hours a conversion of 54.5% (HPLC) is obtained. After refluxing over night (17 h) a conversion of 92% is observed. After 40 h the conversion is >98.5%. Thereafter the reaction is quenched by droping the reaction mixture to cold 2 N hydrochloric acid (50 ml) under stirring to give a white precipitate which is dissolved by addition of 20 ml of acetonitrile to give a clear biphasic solution. The product is extracted with 50 ml of isopropyl acetate. The organic phase is treated with aqueous pottasium carbonate solution (pH 10) until all product is dissolved in the aqueous layer as the potassium salt. Then the basic aqueous phase is adjusted to pH 1-2 by addition of ca. 90 ml of 2N HCl. The product is extracted twice with 50 ml of isopropyl acetate and the organic phase is evaporated under reduced pressure to give after drying in vacuum the very pure, white crystalline product.

Beispiel 2: m.p.: 150-152° C.: (Ref. substance: DiPharma sample: m.p. 149-151° C.) Tlc: $R_f$-value: 0.56 Toluene:EtOAc:AcOH=20:20:1), $SiO_2$-plate (Merck KgaA)

EXAMPLE 4a 5-(4'-Hydroxymethylbiphenyl-2-yl)-1H-tetrazole

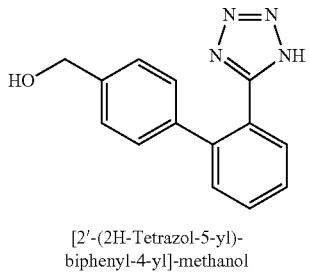 [SMILES: OCc1ccc(-c2ccccc2-c2nnn[nH]2)cc1]

[2'-(2H-Tetrazol-5-yl)-biphenyl-4-yl]-methanol 1.235 g of granular sodium azide (19 mmol) are added to a cold solution of diisobutyl aluminium chloride (19 mmol, 1.8M in toluene) diluted in 5 ml of toluene and the mixture is stirred at room temperature over the night to give diisobutyl aluminium azide.

2.1 g of 4'-hydroxymethyl-biphenyl-2-carbonitrile (10 mmol), are treated, in a drop wise manner at 0° C. with 5.52 ml of triethyl aluminium (10 mmol, 1.8M in toluene). The reaction mixture is stirred for 5 minutes. After that, the clear colourless reaction mixture is added to the solution of diisobutyl aluminium azide (19 mmol), gradually warmed to an internal temperature of about 100° C. and stirred over the night (conversion 95.7%). For the work up the reaction mixture is cooled to 0° C. and added dropwise to a solution of 30 ml of HCl (2 N) containing 1.38 g of $NaNO_2$ (20 mmol) (cooled to 0° C.). 40 ml of iso-propyl acetate are added and the mixture is extracted once with 15 ml of HCl 2N, once with 20 ml of water. The combining aqueous layers are extracted twice with 10 ml of isopropyl acetate. The organic phase is extracted three times with 15 ml portions of an aqueous solution of $K_2CO_3$ (10%). The aqueous phase is washed once with 15 ml of isopropyl acetate. HCl (2 N) is added to the aqueous phase to adjust the pH to 2, and the solution is extracted three times with 20 ml portion of isopropyl acetate. The combining organic phase is washed once with 20 ml of water and the solvent is removed to give the crude product. The crude product is crystallized from ethyl acetate and isopropyl ether to give the pure product.

m.p.: 137-139° C.;

Tlc: Rf-value: 0.21, (toluene:EtOAc:AcOH=20:20:1), $SiO_2$- plates (Merck KgaA)

Catalog-Nr. 1.05628.0001)

EXAMPLE 4b

The reaction as in Example can also be carried out with diethyl aluminium azide at higher concentration and higher temperature.

EXAMPLE 5

Synthesis of 5-((E)-Styryl-2H-tetrazole

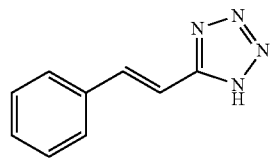 [SMILES: C(=C\c1nnn[nH]1)/c1ccccc1]

Procedure:

To a 50 ml, three necked round bottomed flask, 10 ml of a solution of diisobutyl aluminium fluoride (10 mmol, 1 M in hexane), diluted in 10 ml of toluene, are added. $NaN_3$ is added to the solution (650 mg, 10 mmol), and the mixture is stirred at room temperature for 4h. The stirred solution is cooled at 0° C. with an ice-bath. 0.62 ml of cinnamonitrile (5 mmol) diluted in 3 ml of toluene are added, the mixture is warmed to 90° C. (i.t.) and stirred over the night. The temperature is increased to 105° C. (i.t.) and stirred over the night. After a total time of 70 hours (no complete conversion) the reaction was quenched. The mixture is cooled to −10° C. and treated drop wise with 8 ml of HCl (6N) (pH1). The aqueous phase is extracted with 10 ml of ethyl acetate. The organic phase is washed twice with 10 ml portion of NaCl sat. and then extracted twice with 10 ml portion of $KHCO_3$. The water phase is washed twice with 10 ml portion of ethyl acetate and then treated with HCl to pH 1-2 and extracted three times with ethyl acetate. The organic phase is dried over $Na_2SO_4$ and the solvent removed in vacuum to give after drying the title product.

m.p.: 158-160° C.

Tlc: Rf-value: 0.46 (Toluene:EtOAc:AcOH (20:20:1)

EXAMPLE 6

5-(2-Fluorophenyl)-1H-tetrazole

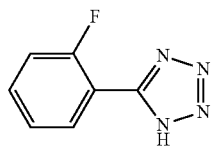 [SMILES: Fc1ccccc1-c1nnn[nH]1]

20 mmol (1.3 g) of sodium azide are charged to a 25 ml flask under argon atmosphere followed by slow addition (via syringe) of 11 ml of a solution of diethyl aluminium chloride (1.8 molar in toluene), 20 mmol, at 0° C. under stirring. The suspension is stirred over night at room temperature. Then 1.8 g (1.2 ml), (15 mmol), 2-fluoro-benzonitrile are added and the mixture is heated at external temperature of 90° C. for 7 hours. After this time the conversion was complete (HPLC). Work up: The reaction mixture is quenched on 20 ml HCl (2 molar) containing 20 mmol $NaNO_2$ at 0° C. to destroy hydrazoic acid which is formed from excess azide. The precipitate which is formed is dissolved by addition of 20 ml acetonitrile to give a clear biphasic solution. The aqueous phase is extracted twice with each 10 ml ethyl acetate. The combined organic phases are extracted with 15 ml of an aqueous solution (10%) of potassium carbonate and adjusted to pH 10. The organic phase is extracted twice with 10 ml of water. The combined aqueous basic phases are neutralized with 2 N HCl and the pH is adjusted to pH 1-2. The product is extracted with ethyl acetate. The ethyl acetate is evaporated under reduced pressure to give a crystalline residue which is further dried in vacuo at 50° C. to give a white crystalline solid.

m.p.: 158-160° C.

Tlc: Rf-value: 0.48 (toluene:EtOAc:AcOH=20:20:1), $SiO_2$-plates

EXAMPLE 7

4'-Hydroxymethyl-biphenyl-2-carbonitrile

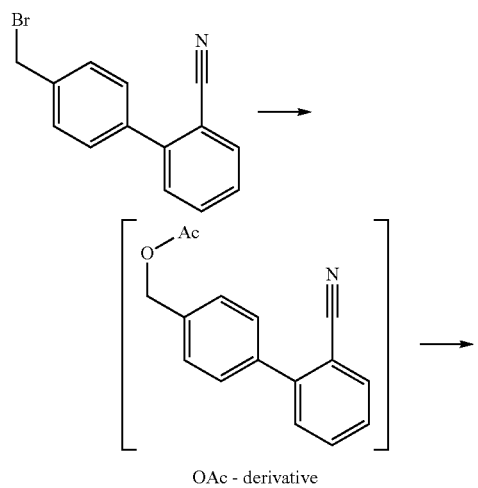

4'-Hydroxymethyl-biphenyl-2-carbonitrile

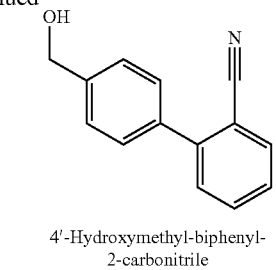

One pot PTC preparation of 4'-hydroxymethyl-biphenyl-2-carbonitrile from 4'-bromomethyl-biphenyl-2-carbonitrile without isolation of the intermediate OAc (O-acetyl) derivative.

A 750 ml flask is charged with 54.4 g (0.2 mol) of 4'-bromomethyl-biphenyl-2-carbonitrile and 250 ml of toluene. To this suspension is added a solution of 30 g (0.3 mol) of potassium acetate in 15 ml of water. The heterogeneous mixture is heated up to an internal temperature of 90° C. to become a clear biphasic solution. After 12 hours at an internal temperature of 90° C. the conversion to the OAc derivative is complete. The biphasic mixture is cooled down to internal temperature of about 50° C. followed by addition of 150 ml NaOH (2N). The mixture is heated up to an internal temperature of ca. 70° C. (extern. temp. 80° C.). After 5 hours at this temperature the PTC saponification is complete (100% conversion, HPLC). Additional 150 ml toluene is added and the warm reaction solution (ca. 50° C.) is washed three times with 50 ml of hot water until the pH is around 7. The toluene phase is evaporated under reduced pressure and the resulting crystalline residue is dried at 50° C. over 24 hours in vacuum to give the white crystalline product with 98% purity (HPLC) and a water content of 0.23%.

m.p.: 118-120° C.

Tlc: Rf-value: 0.45, (toluene:EtOAc:AcOH=20:20:1), $SiO_2$- plate

EXAMPLE 8a 5-(4'-Formyl-biphenyl-2-yl)-1H-tetrazole or 2'-(2H-Tetrazol-5-yl)-biphenyl-4-carbaldehyd 1.01 g (4 mmol) of 5-(4'-hydroxymethylbiphenyl-2-yl)-1H-tetrazole is dissolved in 7 ml of a 10% aqueous solution of potassium carbonate. To the stirred solution is added an aqueous solution (ca. 8%) of sodium hypochlorite (eau de Labarraque) at room temperature. After 40 min. a conversion of 50% to the aldehyde is observed. After 3.5 hours additional 1.5 ml sodium hypochlorite is added at room temperature. After a total reaction time of 7 hours a conversion of >93% is observed. Stirring over night at 0° C. improves the conversion to 97%. The reaction mixture is quenched with 20% aqueous sodium hydrogen sulfite solution (5 ml) under stirring for 1 hour to destroy excess hypochlorite. Then 2-methyl-2-butene (1.5 ml) is added and the product is precipitated by carefully dropping 10 ml of 6 N HCl at 0° C. to the mixture under stirring. The product is extracted with ethyl acetate and the solvent is evaporated to dryness to give the solid product.

m.p.: 184-186° C.

Tlc: Rf-value: 0.31, (toluene:EtOAc:AcOH=20:20:1), SiO$_2$-plate.

EXAMPLE 8b

Compound (VI c), 5-(4'-hydroxymethylbiphenyl-2-yl)-1H-tetrazole, 504 mg (2 mmol) is suspended in a mixture of 2 ml of toluene and 1 ml of dichloromethane. The suspension is cooled to 0° C. and 0.42 ml of nitric acid (ca. 6 mmol), (65%, d=1.4) is added in one portion at 0° C. under stirring which results in a clear slightly yellow solution. The ice bath is removed and stirring is continued at room temperature for ca. 1 h. After 1 h the product (VI) is crystallizing directly from the reaction mixture. The slurry is cooled to 0° C. for 1 h and then filtered to give after drying in vacuum 400 mg of pure aldehyde (VI).

EXAMPLE 9

5-(2-Chlorophenyl)-1H-tetrazole (with dibutylboron azide)

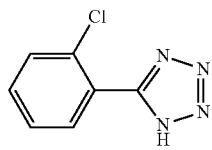

A dry 25 ml flask is charged with 10 ml (10 mmol) of a heptane solution of dibutyl boryl triflate (1 molar) under Argon. To this solution is added 650 mg (10 mmol) of sodium azide. The suspension is stirred over night at room temperature to give a dibutylboron azide. To the suspension is added 1.0 g (7.7 mmol) 2-chlorobenzo nitrile as a solid in one portion. The reaction mixture is heated up to 130° C. external temperature. After 5 hours the conversion to the desired product is only 5%. Additional 5 ml of toluene is added and refluxing is continued over night. After 24 hours the conversion is 27%. After additional 24 h refluxing at 130° C. (ext. temp.) the conversion is 35% (HPLC). The reaction is stopped by carefully quenching the yellow suspension on 6 N HCl. The product is extracted to the water phase with 2×10 ml of potassium carbonate solution. The water layer is adjusted to pH 1 with 6N HCl and the product is extracted with ethyl acetate. The solvent is evaporated to dryness to give an off-white solid residue.

Tlc: R$_f$-value: 0.48, toluene:EtOAc:AcOH (20:20:1); SiO$_2$-plate.

EXAMPLE 10

5-(4-Chlorophenyl)-1H-tetrazole

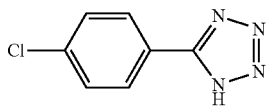

Procedure:

292 mg of granular sodium azide (4.5 mmol) are added to a cold solution of diethyl aluminum chloride (4.5 mmol, 1.8 M in toluene) diluted in 2.5 ml of toluene, and the mixture is stirred at room temperature for 4 h. 473 mg of 4-Chlorobenzonitrile are added to the stirred solution, and the reaction mixture is heated up to 135° C. (e.t.) and stirred over the night. Complete conversion is observed by HPLC. 5 ml of toluene are added to the mixture, then the solution is added drop wise to a cold solution of HCl 6N. 10 ml of ethyl acetate are added and the solution extracted. The aqueous phase is washed twice with 10 ml portion of ethyl acetate. The combined organic phases are washed with 10 ml portion of HCl 2N and finally with 10 ml of water. The solvent is removed and the product is dried in vacuum at 60° C. over the night to give the product.

m.p.: 255-257° C.

Tlc: R$_f$-value: 0.40, toluene:EtOAc:AcOH (20:20:1); SiO$_2$-plate.

HPLC: Hewlett Packard, solvents. H$_3$PO$_4$, acetonitrile/water; flow: 2 ml/min; injection: 5.0 µl; wavelength 220 nm, 40° C.; flow: 2 ml/min; injection: 5.0 µl; Column: Merck, Chromolith Performance RP-18e 100-4.6 mm. Rt. Time: 6.184 min

EXAMPLES 11a) to 11l)

The following table (Examples 11a) to 11l) should further illustrate the present invention. When applying the method of the present invention, tetrazole compounds of formula (I) are obtainable starting from nitrile compounds of formula (II a):

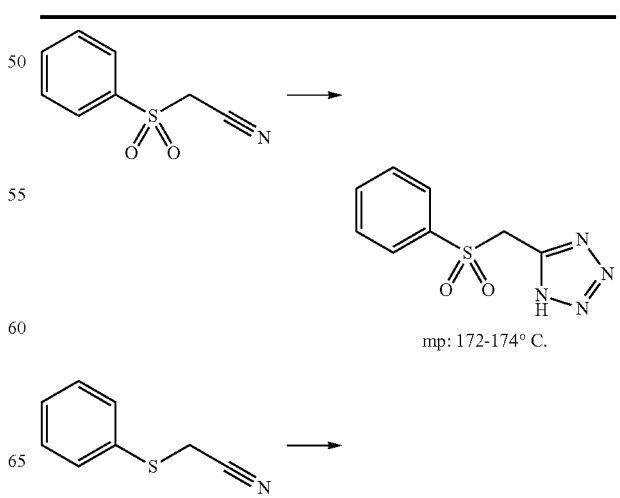

mp: 172-174° C.

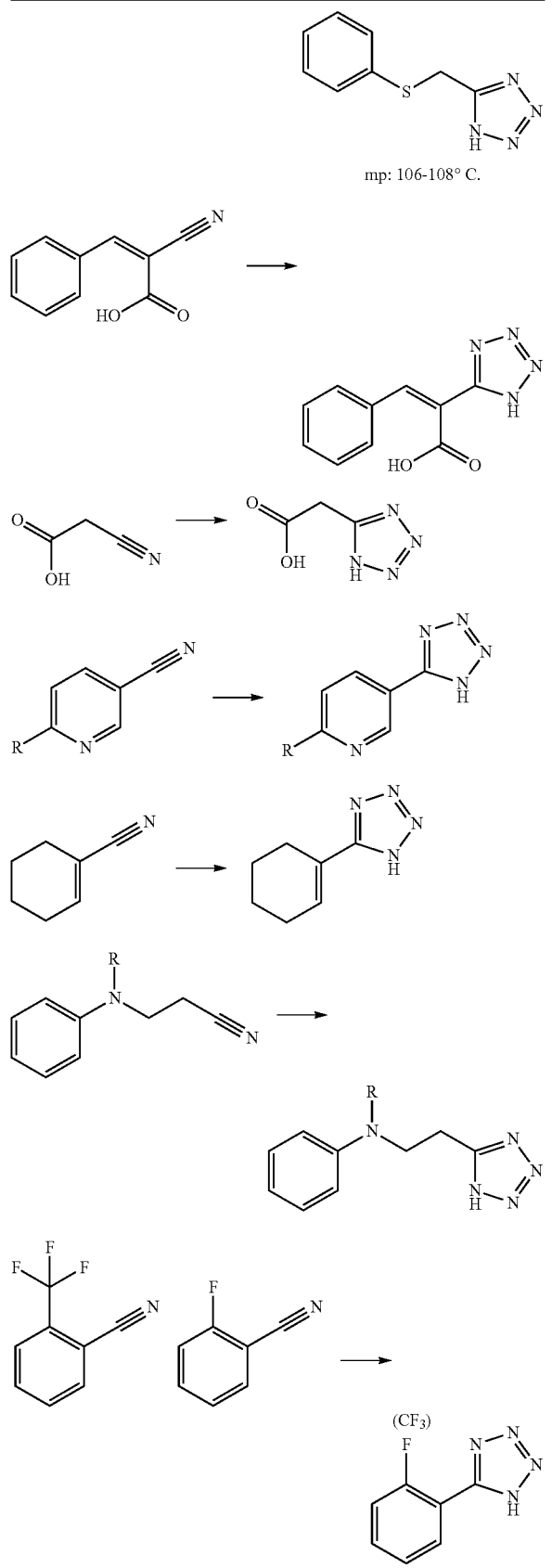
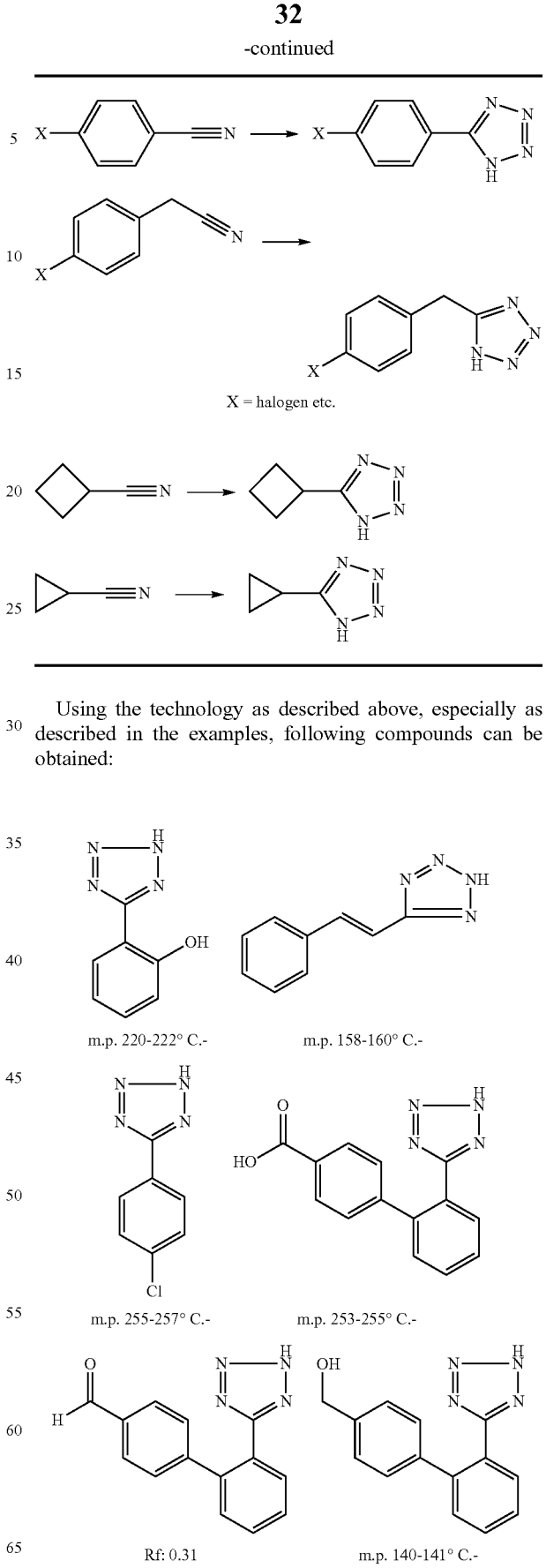
Using the technology as described above, especially as described in the examples, following compounds can be obtained:

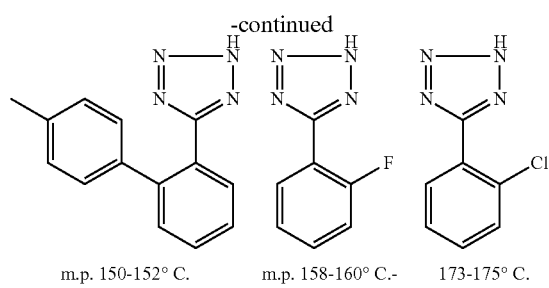

m.p. 150-152° C.    m.p. 158-160° C.-    173-175° C.

EXAMPLE 12

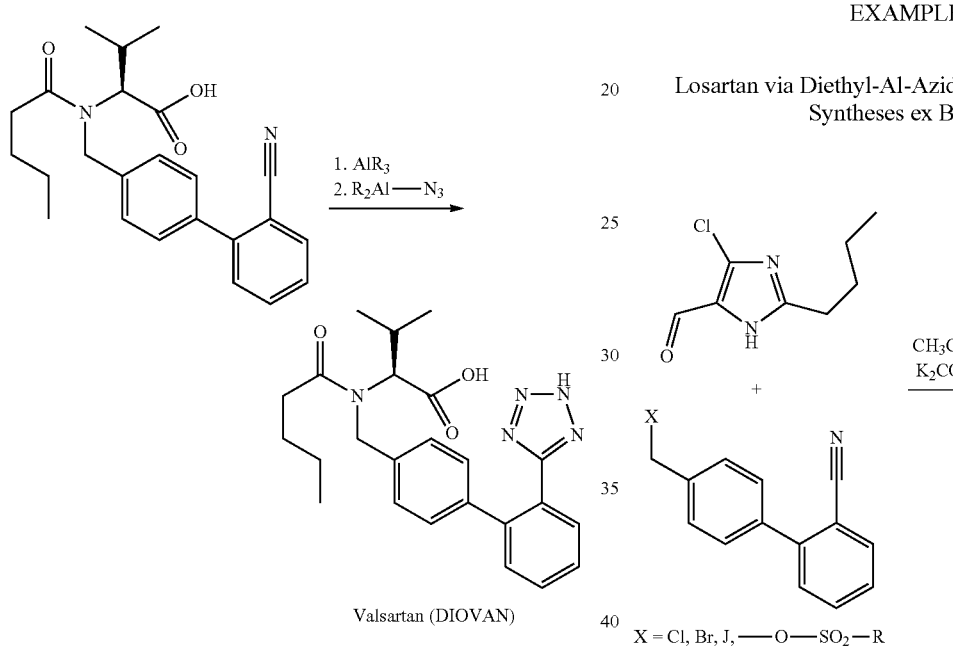

Valsartan (DIOVAN)

A suspension of 5 mmol of formula 1.96 g 5 mmol), in 5 ml of toluene and 2.7 ml of a 1.8 molar solution of triethyl aluminium in dry toluene are slowly combined at 0° C. The separately prepared diisobutyl-Al-azid (7 mmol) in toluene is added to the suspension and finally the mixture is heated to an internal temperature of ca. 110° C. over night. HPLC control shows after 14 h ca. 50% conversion. Another portion of diisobutyl aluminium azid (4 mmol) is added and heating at reflux temperature at 130° C. is continued for further 12 hours. HPLC shows a conversion of ca. 77% to the desired product (Valsartan DS) and ca. 23% of starting material. After cooling down to room temperature the reaction mixture was quenched onto a mixture of an aqueous solution of 50 mmol of $NaNO_2$ in 40 ml of 2N hydrochloric acid. Additional 20 ml of 2N HCl is added under stirring to dissolve precipitated aluminium hydroxide. Finally the product is isolated from the aqueous phase by extraction with i-propyl acetate. The combined organic phases (toluene/i-PrOAc) are washed with 30 ml of water and evaporated to dryness in vacuum to give crude oily valsartan which contained still ca. 23% of starting material. The product can be purified by careful extraction with $KHCO_3$ from the organic phase to the aqueous phase as the bis potassium salt and subsequent adjustment with hydrochloric acid and back extraction to i-propyl acetate.

EXAMPLE 13

Losartan via Diethyl-Al-Azid-Cycloaddition 3 Step Syntheses ex Br-OTBN

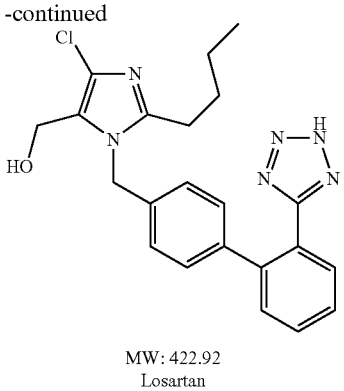

MW: 422.92
Losartan

Reaction Step 1: Disclosed in

1) K. Srinivas et al., Synthesis, 2004, (4), 506

2) R. D. Larsen et al., J. Org. Chem., 59, 6391 (1994)

3) T. Kato & Y. Shida, EP 578125 A1 (19940112)

Reaction Step 2. Reduction of the aldehyde with NaBH$_4$ to form the corresponding alcohol:I 3.78 g (10 mmol) of "5-formyl-imidazol-1-ylmethyl-biphenyl-2-carbonitrile" are suspended in 50 ml of ethanol. To this suspension is added in 2 portions 152 mg (4 mmol) of NaBH$_4$ under stirring at 10° C. After stirring for 2-3 hours the reaction is quenched by addition of 10 ml 2N HCl. The reaction mixture is concentrated in vacuum and finally diluted with 25 ml of water. The aqueous phase is extracted 3 times with 30 ml of ethyl acetate. The organic phases are combined and evaporated to dryness to give an almost white solid residue which is dried in vacuum. The crude "alcohol" is used in the next step without further purification.

Reaction Step 3. Example for "in-situ-protection" with AlEt$_3$ and subsequent cycloaddition with diethyl-Al-azide and working up to LOSARTAN.

1.9 g (5 mmol) of the "hydroxymethyl-imidazol-1-ylmethyl biphenylcarbonitrile" from the previous step is suspended in 10 ml of dry toluene under argon. To this suspension is added at room temperature under stirring 2.8 ml of a 1.8 molar solution of AlEt$_3$ in toluene. Stirring of the suspension was continued for additional 3 hours. Then a solution of 10 mmol diethyl aluminium azide in toluene, which is prepared in a separate flask, is added via syringe. (This 10 mmol of Et$_2$Al—N$_3$ was prepared by stirring 10 mmol of Et$_2$AlCl and 10 mmol of NaN$_3$ in toluene at room temperature over night to give a white suspension of NaCl, but the diethyl aluminium azide is dissolved in toluene). The rection mixture is heated to reflux (~111° C.), external temperature ca. 140° C. conversion is controlled by HPLC analysis. After refluxing for 24 hours the reaction mixture was cooled to room temperature and finally quenched on an aqueous solution of 40 mmol of NaNO$_2$ in 40 ml of 2N hydrochloric acid. Then additional 20 ml of 2N HCl is added under stirring to dissolve the precipitated Aluminium hydroxide. Finally the product was isolated from the aqueous phase by extraction with ethyl acetate. The combined organic phases (toluene/EtOAc) are washed 2 times with 25 ml of water and evaporated to dryness in vacuum to give crude Losartan. The crude Losartan can be purified by crystallization from CH$_3$CN or CH$_3$CN /water mixtures, according to literature; (J.O.C., 59, 6391 (1994)).

EXAMPLE 14

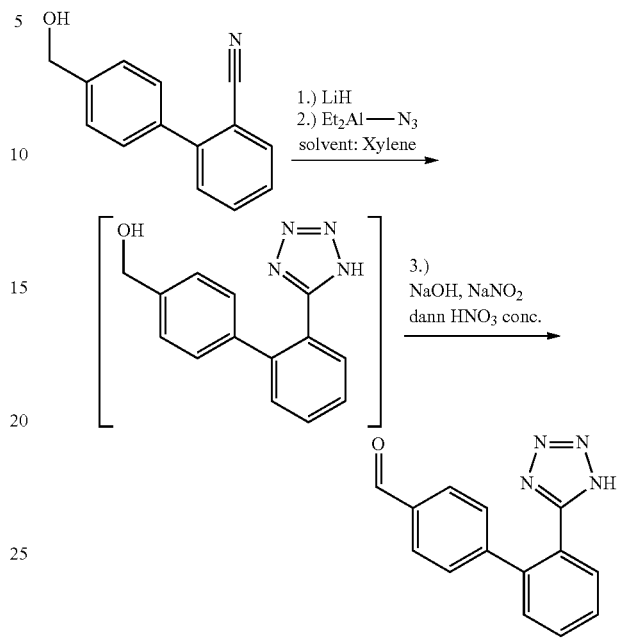

16.74 g (80 mmol) of the "4-hydroxymethyl-biphenyl-2-carbonitrile" is suspended in 100 ml of dry xylene (isomer mixture) under argon. To this suspension is added at room temperature under stirring 0.636 g (80 mmol) of lithium hydride. The suspension is stirred for an additional 4 hours at 120° C. external temperature and a solution of 160 mmol diethylaluminium azide in toluene (which is prepared separately by stirring 160 mmol of diethylaluminium chloride and 160 mmol of sodium azide in xylene [isomer mixture] at room temperature overnight) is added via syringe. The reaction mixture is heated to reflux (~120° C.), external temperature ca. 140° C. Conversion is controlled by HPLC analysis. After refluxing for 24 hours the reaction mixture is cooled to room temperature and finally quenched with a solution of 300 mmol of sodium nitrite and of 15% sodium hydroxide (240 mmol). Finally 95 ml of conc. HCl is added under stirring. To the resulting suspension is added at room temperature under stirring 31 g (320 mmol) of 65% nitric acid. The suspension is stirred for an additional 6 hours at 60° C. external temperature (internal Temperature=55° C.). Finally the product is isolated by filtration. The crude 2'-(1H-tetrazol-5-yl)-biphenyl-4-carbaldehyde is obtained.

What is claimed is:

1. A compound of formula (R$_1$)(R$_2$)M-N$_3$ (II b), wherein M is aluminium or boron; and each one of R$_1$ and R$_2$, independently of one another, is C$_3$-C$_7$alkenyl, C$_3$-C$_7$-cycloalkyl, phenyl-C$_1$-C$_4$-alkyl, phenyl-C$_3$-C$_5$alkenyl, or C$_3$-C$_8$-cycloalkyl-C$_1$-C$_8$-alkyl.

2. The compound of claim 1, wherein the C$_3$-C$_7$ alkenyl is allyl or crotyl.

3. The compound of claim 1, wherein the C$_3$-C$_7$-cycloalkyl is cyclohexyl.

4. The compound of claim 1, wherein the phenyl-C$_1$-C$_4$-alkyl is benzyl or 2-phenethyl.

5. The compound of claim 1, wherein the phenyl-C$_3$-C$_5$alkenyl is cinnamyl.

6. The compound of claim 1, wherein the $C_3$-$C_8$-cycloalkyl-$C_1$-$C_8$-alkyl is cyclopropylmethyl or cyclohexylmethyl.

7. The compound of claim 1, wherein each one of $R_1$ and $R_2$, independently of one another, is allyl, crotyl, cyclohexyl, benzyl, 2-phenethyl, cinnamyl, cyclopropylmethyl or cyclohexylmethyl.

* * * * *